US012661519B2

(12) United States Patent
Zhang et al.

(10) Patent No.: US 12,661,519 B2
(45) Date of Patent: Jun. 23, 2026

(54) METHOD AND APPARATUS FOR DETECTING LEAD MIGRATION USING PHYSIOLOGICAL SIGNAL

(71) Applicant: Boston Scientific Neuromodulation Corporation, Valencia, CA (US)

(72) Inventors: Tianhe Zhang, Studio City, CA (US); Changfang Zhu, Valencia, CA (US); Rosana Esteller, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1119 days.

(21) Appl. No.: 17/689,448

(22) Filed: Mar. 8, 2022

(65) Prior Publication Data

US 2022/0323777 A1 Oct. 13, 2022

Related U.S. Application Data

(60) Provisional application No. 63/173,748, filed on Apr. 12, 2021.

(51) Int. Cl.
*A61N 1/372* (2006.01)
*A61N 1/05* (2006.01)
*A61N 1/36* (2006.01)

(52) U.S. Cl.
CPC ....... *A61N 1/37247* (2013.01); *A61N 1/0551* (2013.01); *A61N 1/36139* (2013.01)

(58) Field of Classification Search
CPC .............. A61N 1/0551; A61N 1/36139; A61N 1/36142; A61N 1/37247
See application file for complete search history.

(56) References Cited

U.S. PATENT DOCUMENTS

| 6,993,384 B2 | 1/2006 | Bradley et al. |
| 8,233,992 B2 | 7/2012 | Zhu et al. |

(Continued)

FOREIGN PATENT DOCUMENTS

| WO | WO-2018080753 A1 | 5/2018 |
| WO | WO-2020087123 A1 | 5/2020 |

(Continued)

OTHER PUBLICATIONS

"Australian Application Serial No. 2022258017, First Examination Report mailed Aug. 15, 2024", 2 pgs.

(Continued)

*Primary Examiner* — Pamela M. Bays
*Assistant Examiner* — Shreya Anjaria
(74) *Attorney, Agent, or Firm* — Schwegman Lundberg & Woessner, P.A.

(57) ABSTRACT

An example of a neurostimulation system may include a programming control circuit, a sensing circuit, and a stimulation control circuit. The programming control circuit may be configured to generate stimulation parameters controlling delivery of neurostimulation according to stimulation waveform(s) and stimulation field(s). The sensing circuit may be configured to sense signals. The stimulation control circuit may be configured to determine the stimulation waveform(s) and the stimulation field(s) based on a lead configuration and may be configured to determine first and second electrodes of respective first and second leads, receive first and second signals sensed using the first and second electrodes, detect corresponding signal features from the first and second signals, determine a feature delay between the detected signal features, and determine a need for adjusting the lead configuration using the feature delay. The signal features are associated with a response of the patient to the neurostimulation.

20 Claims, 17 Drawing Sheets

(56)  References Cited

U.S. PATENT DOCUMENTS

| | | | |
|---|---|---|---|
| 8,738,155 B2 | 5/2014 | Zhu et al. | |
| 9,089,705 B2 | 7/2015 | Zhu | |
| 9,259,589 B2 | 2/2016 | Goetz et al. | |
| 9,302,112 B2 | 4/2016 | Bornzin et al. | |
| 10,744,323 B2 | 8/2020 | Hamacher et al. | |
| 10,926,092 B2 | 2/2021 | Esteller et al. | |
| 2006/0224222 A1* | 10/2006 | Bradley | A61N 1/3614 |
| | | | 607/116 |
| 2012/0065702 A1* | 3/2012 | Arcot-Krishnamurthy | |
| | | | A61N 1/36053 |
| | | | 607/48 |
| 2014/0163639 A1* | 6/2014 | Zhu | A61B 5/7221 |
| | | | 607/46 |
| 2014/0277282 A1* | 9/2014 | Jaax | A61N 1/36139 |
| | | | 607/59 |
| 2020/0001096 A1 | 1/2020 | Zhang et al. | |

FOREIGN PATENT DOCUMENTS

| | | | |
|---|---|---|---|
| WO | WO-2020223165 A1 | 11/2020 | |
| WO | WO-2022220956 A1 | 10/2022 | |

OTHER PUBLICATIONS

"European Application Serial No. 22712742.0, Response to Communication Pursuant to Rules 161 and 162 EPC Filed Apr. 30, 2024", 21 pgs.

"International Application Serial No. PCT/US2022/019288, International Preliminary Report on Patentability mailed Oct. 26, 2023", 8 pgs.

"International Application Serial No. PCT/US2022/019288, International Search Report mailed Jun. 14, 2022", 5 pgs.

"International Application Serial No. PCT/US2022/019288, Written Opinion mailed Jun. 14, 2022", 6 pgs.

Zhang, Tianhe, et al., "Adjustment of Stimulation in Response to Electrode Array Movement in a Spinal Cord Stimulator System", U.S. Appl. No. 62/840,534, filed Apr. 30, 2019.

"Australian Application Serial No. 2022258017, Response filed Mar. 31, 2025 to First Examination Report mailed Aug. 15, 2024", 6 pgs.

* cited by examiner

100

960

REFLECTION

CENTRAL POINT OF STIMULATION

USER-DEFINED

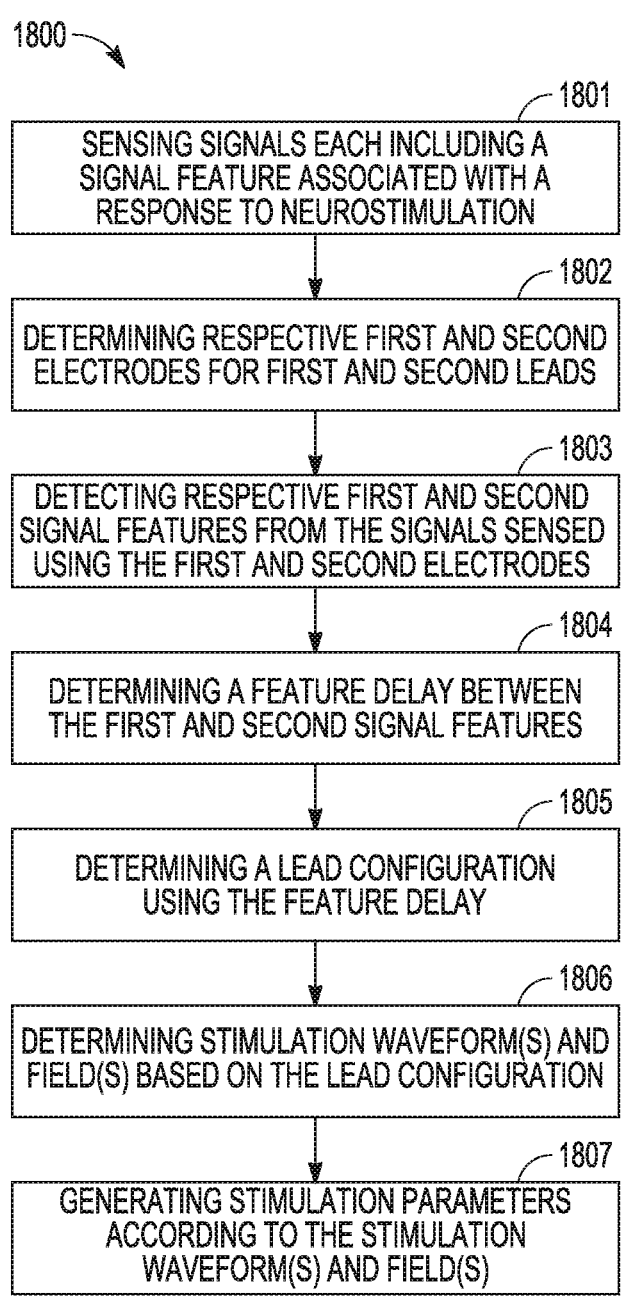

1800

1801
SENSING SIGNALS EACH INCLUDING A SIGNAL FEATURE ASSOCIATED WITH A RESPONSE TO NEUROSTIMULATION

1802
DETERMINING RESPECTIVE FIRST AND SECOND ELECTRODES FOR FIRST AND SECOND LEADS

1803
DETECTING RESPECTIVE FIRST AND SECOND SIGNAL FEATURES FROM THE SIGNALS SENSED USING THE FIRST AND SECOND ELECTRODES

1804
DETERMINING A FEATURE DELAY BETWEEN THE FIRST AND SECOND SIGNAL FEATURES

1805
DETERMINING A LEAD CONFIGURATION USING THE FEATURE DELAY

1806
DETERMINING STIMULATION WAVEFORM(S) AND FIELD(S) BASED ON THE LEAD CONFIGURATION

1807
GENERATING STIMULATION PARAMETERS ACCORDING TO THE STIMULATION WAVEFORM(S) AND FIELD(S)

FIG. 18

METHOD AND APPARATUS FOR DETECTING LEAD MIGRATION USING PHYSIOLOGICAL SIGNAL

CLAIM OF PRIORITY

This application claims the benefit of U.S. Provisional Application No. 61/173,748, filed on Apr. 12, 2021, which is hereby incorporated by reference in its entirety.

TECHNICAL FIELD

This document relates generally to implantable medical devices and more particularly to a method and system for detecting migration of one or more implantable leads using a sensed physiological signal.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered to a patient in a form of electrical pulses. The delivery is controlled using stimulation parameters that specify spatial (where to stimulate), temporal (when to stimulate), and informational (patterns of pulses directing the nervous system to respond as desired) aspects of a pattern of the electrical pulses. The spatial aspects include locations of electrodes and distribution of the neurostimulation energy over the electrodes. When the neurostimulation is delivered from an implantable neurostimulator through one or more implantable leads placed in the patient, the locations of the electrodes may change over time as the one or more implantable leads migrate in tissue after their initial placement. Such lead migration may necessitate adjustment of the stimulation parameters to maintain efficacy, efficiency, and/or safety of a neurostimulation therapy.

SUMMARY

An Example (e.g., "Example 1") of a system for delivering neurostimulation to a patient through a plurality of electrodes using first and second leads each including one or more electrodes of the plurality of electrodes is provided. The system may include a programming control circuit, a sensing circuit, and a stimulation control circuit. The programming control circuit may be configured to generate stimulation parameters controlling delivery of the neurostimulation according to one or more stimulation waveforms and one or more stimulation fields. The one or more stimulation fields each specify a distribution of a stimulation energy over the plurality of electrodes. The sensing circuit may be configured to sense signals using sensing electrodes selected from the plurality of electrodes. The stimulation control circuit may be configured to determine the one or more stimulation waveforms and the one or more stimulation fields based on a lead configuration including positions of the plurality of electrodes. The stimulation control circuit may include a lead configuration circuit that may be configured to determine a first electrode of the first lead and a second electrode of the second lead, receive a first signal sensed using the first electrode and a second signal sensed using the second electrode, detect a first signal feature from the first signal and a second signal feature from the second signal, determine a feature delay being a time interval between the detected first and second signal features, and determine a need for adjusting the lead configuration using the feature delay. The first and second signal features are associated with a response of the patient to the neurostimulation.

In Example 2, the subject matter of Example 1 may optionally be configured such that the sensing circuit is configured to sense neural signals including evoked compound action potentials (ECAPs), and the lead configuration circuit is configured to detect an ECAP feature from each of the first and second neural signals as the respective first and second signal features.

In Example 3, the subject matter of any one or any combination of Examples 1 and 2 may optionally be configured such that the lead configuration circuit is configured to perform an initial calibration for determining the lead configuration using the feature delay. The initial calibration includes determining and confirming a selection for the first and second electrodes and determining and confirming a selection for the first and second signal features.

In Example 4, the subject matter of Example 3 may optionally be configured to further include a user interface configured to present the lead configuration and to receive user input for at least one of selecting the first and second electrodes or selecting the first and second signal features.

In Example 5, the subject matter of any one or any combination of Examples 3 and 4 may optionally be configured such that the lead configuration circuit is configured to perform measurements automatically for the initial calibration, the measurements determining at least the feature delay.

In Example 6, the subject matter of any one or any combination of Examples 1 to 5 may optionally be configured such that the lead configuration circuit is configured to determine a conduction velocity using the detected first and second signal features, determine the feature delay, calculate an offset distance between the first and second electrodes by multiplying the determined conduction velocity by the determine feature delay, and determine the lead configuration using the offset distance.

In Example 7, the subject matter of Example 6 may optionally be configured such that the lead configuration circuit is configured to compare the calculated offset distance to a specified tolerance, recommend a re-alignment option in response to the determined offset distance exceeding the specified tolerance, present a warning message in response to the recommendation not being accepted, and automatically update the lead configuration using the calculated offset distance in response to the recommendation being accepted.

In Example 8, the subject matter of any one or any combination of Examples 6 and 7 may optionally be configured such that the lead configuration circuit is configured to assess reliability of the measurements by determining the offset distance by at least one of repeated determination using a single method of determining the offset distance or repeated determination using multiple methods of determining the offset distance and comparing results obtained from determining the offset distance using the multiple methods.

In Example 9, the subject matter of Example 8 may optionally be configured such that the lead configuration circuit is configured to determine a morphological parameter of each of the neural signals sensed using the first and second electrodes, calculate the offset distance using the determined morphological parameter and template morphological parameter, and assess reliability of the calculated offset distance by comparing the offset distance calculated using the feature delay and the offset distance calculated using the morphological parameter.

In Example 10, the subject matter of any one or any combination of Examples 8 and 9 may optionally be configured such that the lead configuration circuit is configured to assess a likelihood of lead migration that has actually occurred.

In Example 11, the subject matter of any one or any combination of Examples 8 and 9 may optionally be configured such that the lead configuration circuit is configured to assess a reliability of the calculated offset distance.

In Example 12, the subject matter of any one or any combination of Examples 8 to 13 may optionally be configured such that the lead configuration circuit is configured to produce a recommendation for adjustment of at least one of the one or more stimulation waveforms or the one or more stimulation fields based on the assessed reliability of the measurements.

In Example 13, the subject matter of any one or any combination of Examples 6 to 12 may optionally be configured such that the lead configuration circuit is configured to automatically adjust the lead configuration in response to the offset distance exceeding a specified tolerance.

In Example 14, the subject matter of any one or any combination of Examples 6 to 12 may optionally be configured such that the lead configuration circuit is configured to present at least one of a warning message or a recommendation for adjusting the lead configuration in response to the offset distance exceeding a specified tolerance.

In Example 15, the subject matter of any one or any combination of Examples 1 to 14 may optionally be configured such that the lead configuration circuit is configured to monitor migration of at least one of the first and second leads based on values of the offset distance determined over time.

An example (e.g., "Example 16") of a method for delivering neurostimulation to a patient through a plurality of electrodes using first and second leads each including one or more electrodes of the plurality of electrodes is also provided. The method may include sensing signals using a sensing circuit and sensing electrodes selected from the plurality of electrodes and generating a plurality of stimulation parameters controlling delivery of the neurostimulation according to one or more stimulation waveforms and one or more stimulation fields using one or more processors. The signals each include a signal feature associated with a response of the patient to the neurostimulation. The one or more stimulation fields each specify a distribution of a stimulation energy over the plurality of electrodes. The generation of the plurality of stimulation parameters may include determining a pair of respective first and second electrodes for the first and second leads, detecting respective signal features from the signals sensed using the first and second electrodes, determining a feature delay being a time interval between the detected respective signal features, determining a lead configuration including positions of the plurality of electrodes using the feature delay, and determining the one or more stimulation waveforms and the one or more stimulation fields based on the lead configuration.

In Example 17, the subject matter of sensing signals as found in Example 16 may optionally include sensing neural signals including evoked compound action potentials (ECAPs), and the subject matter of detecting respective signal features from the neural signals sensed using the first and second electrodes as found in Example 16 may optionally include detecting respective ECAP features from the neural signals sensed using the first and second electrodes.

In Example 18, the subject matter of any one or any combination of Examples 16 and 17 may optionally include performing an initial calibration for determining the lead configuration using the feature delay. The performance of the initial calibration includes determining and confirming a selection for the first and second electrodes and determining and confirming a selection for the first and second signal features.

In Example 19, the subject matter of performing the initial calibration as found in Example 18 may optionally include determining a conduction velocity using the detected first and second signal features, determining the feature delay, calculating an offset distance between the first and second electrodes by multiplying the determined conduction velocity by the determined feature delay, and determining the lead configuration using the offset distance.

In Example 20, the subject matter of performing the initial calibration as found in Example 19 may optionally further include comparing the calculated offset distance to a specified tolerance, recommending a re-alignment option in response to the determined offset distance exceeding the specified tolerance, presenting a warning message in response to the recommendation not being accepted, and automatically updating the lead configuration using the calculated offset distance in response to the recommendation being accepted.

In Example 21, the subject matter of any one or any combination of Examples 19 and 20 may optionally further include assessing reliability of the measurements by determining the offset distance using at least one of repeated determination using a single method of determining the offset distance or repeated determination using multiple methods of determining the offset distance and comparing results obtained from determining the offset distance using the at least one of the repeated determination using the single method or the repeated determination using the multiple methods.

In Example 22, the subject matter of assessing reliability of the measurements as found in Example 21 may optionally include assessing at least one of a likelihood of lead migration that has actually occurred or a reliability of the calculated offset distance.

In Example 23, the subject matter of any one or any combination of Examples 21 and 22 may optionally further include producing a recommendation for adjustment of at least one of the one or more stimulation waveforms or the one or more stimulation fields based on the assessed reliability of the measurements.

In Example 24, the subject matter of any one or any combination of Examples 29 to 32 may optionally further include repeating the determination of the conduction velocity, the determination of the feature delay, and the calculation of the offset distance using selection of the first and second electrodes and the selection of the first and second signal features determined and confirmed during the initial calibration, and monitoring migration of at least one of the first and second leads based on values of the offset distance calculated over time.

An example (e.g., "Example 25") of a non-transitory computer-readable storage medium including instructions, which when executed by a system, cause the system to perform a method for delivering neurostimulation to a patient through a plurality of electrodes using first and second leads each including one or more electrodes of the plurality of electrodes. The method may include sensing signals using a sensing circuit and sensing electrodes selected from the plurality of electrodes and generating a plurality of stimulation parameters controlling delivery of the neurostimulation according to one or more stimulation waveforms and one or more stimulation fields using one or more processors. The signals each include a signal feature associated with a response of the patient to the neurostimulation. The one or more stimulation fields each specify a distribution of a stimulation energy over the plurality of electrodes. The generation of the plurality of stimulation parameters may include determining a pair of respective first and second electrodes for the first and second leads, detecting respective signal features from the signals sensed using the first and second electrodes, determining a feature delay being a time interval between the detected respective signal features, determining a lead configuration including positions of the plurality of electrodes using the feature delay, and determining the one or more stimulation waveforms and the one or more stimulation fields based on the lead configuration.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

FIG. 18 illustrates an embodiment of a method for detecting lead migration and adjusting neurostimulation based on the detection.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized, and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a neurostimulation system that delivers neurostimulation to a patient through electrodes on one or more implantable leads and detects migration of the one or more implantable leads in tissue over time after the initial placement. Depending on the amount of displacement of the electrodes from their original positions, such lead migration may significantly reduce therapeutic effectiveness of the neurostimulation and/or increase magnitude of side effects. Consequently, settings of the implantable stimulation device in the patient may need to be adjusted. The present subject matter detects migration of the one or more implantable leads using signals sensed using electrodes on the one or more implantable leads. The signals include features responding to the neurostimulation and having measurable characteristics indicating positions of the electrodes. For example, difference in amplitude and/or timing of a signal feature between measurements performed at different times can be used to quantitatively assess displacement of an electrode and/or offset distance between electrodes over time. While implantable leads with electrodes for delivery electrical pulses is discussed as an example, the present subject matter can be applied to detect migration of implanted transducers for delivering various types of neurostimulation energy based on sensed signals indicative of physiological responses of the patient to the neurostimulation.

In this document, a "patient" includes a person receiving treatment delivered using a neurostimulation system according to the present subject matter, and a "user" includes a physician or other caregiver who treats the patient using the neurostimulation system. In this document, a "measurement" includes a direct measurement, an indirect measurement (e.g., by calculation using measured, estimated, and/or other known value(s)), and/or an estimation.

Figure 1:
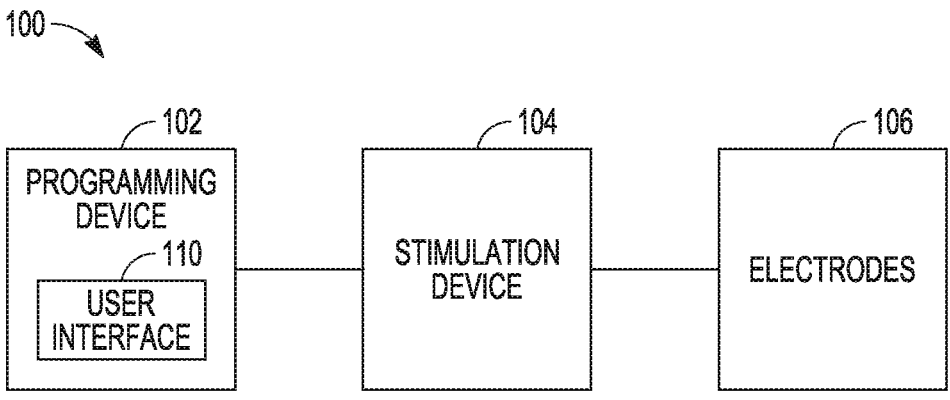
FIG. 1 illustrates an embodiment of a neurostimulation system.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In various embodiments, programming device 102 can include a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 can include a graphical user interface (GUI) that allows the user to set and/or adjust the values of the user-programmable parameters by creating and/or editing graphical representations of various waveforms. Such waveforms may include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

In various embodiments, system 100 can be configured for neurostimulation applications. User interface 110 can be configured to allow the user to control the operation of system 100 for neurostimulation. For example, system 100 as well as user interface 100 can be configured for spinal cord stimulation (SCS) applications. Such SCS configuration includes various features that may simplify the task of the user in programming stimulation device 104 for delivering SCS to the patient, such as the features discussed in this document.

Figure 2:
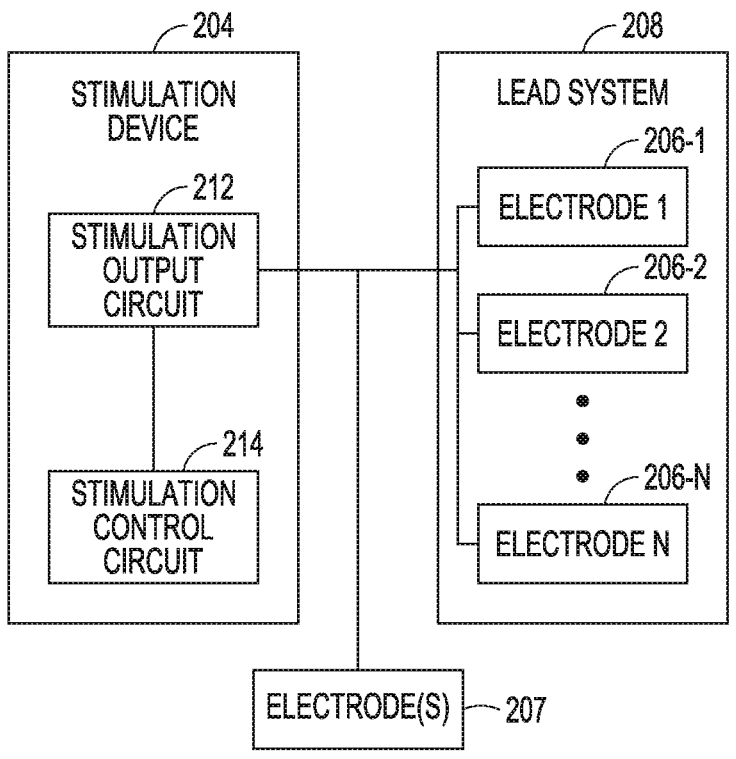
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an example of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses from stimulation output circuit 212 using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses or each of collections of pulse intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none electrode(s) 207. Multipolar stimulation uses a multipolar electrode configuration with multiple (two or more) electrodes selected from electrodes 206 and none of electrode(s) 207.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

Figure 3:
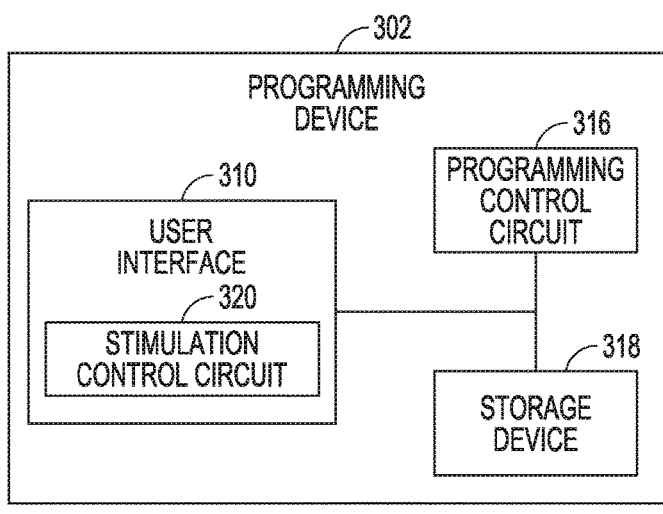
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an example of programming device 102 and includes a storage device 318, a programming control circuit 316, and a user interface 310. Programming control circuit 316 generates the plurality of stimulation parameters that controls the delivery of the neurostimulation pulses according to a specified neurostimulation program that can define, for example, stimulation waveform and electrode configuration. User interface 310 represents an example of user interface 110 and includes a stimulation control circuit 320. Storage device 318 stores information used by programming control circuit 316 and stimulation control circuit 320, such as information about a stimulation device that relates the neurostimulation program to the plurality of stimulation parameters. In various embodiments, stimulation control circuit 320 can be configured to support one or more functions allowing for programming of stimulation devices, such as stimulation device 104 including its various embodiments as discussed in this document, according to one or more selected neurostimulation programs as discussed in this document.

In various embodiments, user interface 310 can allow for definition of a pattern of neurostimulation pulses for delivery during a neurostimulation therapy session by creating and/or adjusting one or more stimulation waveforms using a graphical method. The definition can also include definition of one or more stimulation fields each associated with one or more pulses in the pattern of neurostimulation pulses. As used in this document, a "neurostimulation program" can include the pattern of neurostimulation pulses including the one or more stimulation fields, or at least various aspects or parameters of the pattern of neurostimulation pulses including the one or more stimulation fields. In various embodiments, user interface 310 includes a GUI that allows the user to define the pattern of neurostimulation pulses and perform other functions using graphical methods. In this document, "neurostimulation programming" can include the definition of the one or more stimulation waveforms, including the definition of one or more stimulation fields.

In various embodiments, circuits of neurostimulation 100, including its various embodiments discussed in this document, may be implemented using a combination of hardware and software. For example, the circuit of user interface 110, stimulation control circuit 214, programming control circuit 316, and stimulation control circuit 320, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
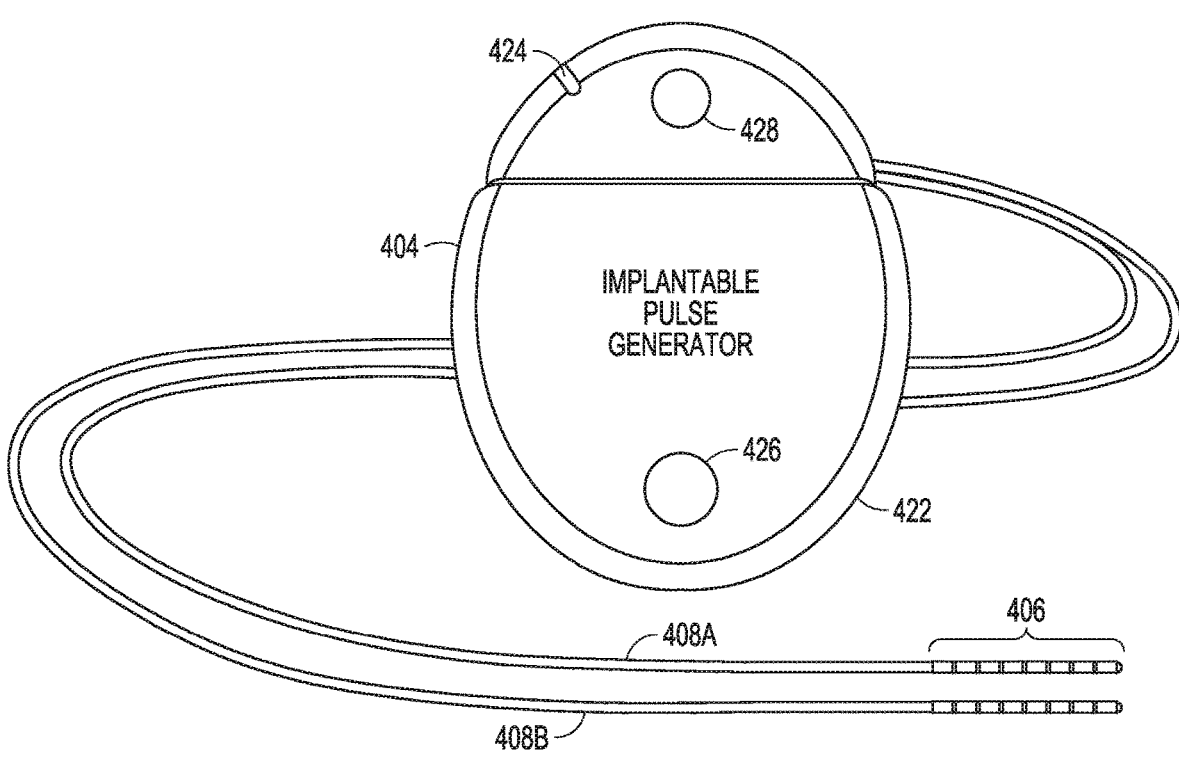
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrical contacts or electrodes 406 for contacting a tissue site targeted for electrical neurostimulation. As illustrated in FIG. 1, leads 408A and 408B each include 8 electrodes 406 at the distal end. The number and arrangement of leads 408A and 408B and electrodes 406 as shown in FIG. 1 are only an example, and other numbers and arrangements are possible. In various embodiments, the electrodes are ring electrodes. The implantable leads and electrodes may be configured by shape and size to provide electrical neurostimulation energy to a neuronal target included in the subject's brain or configured to provide electrical neurostimulation energy to a nerve cell target included in the subject's spinal cord.

Figure 5:
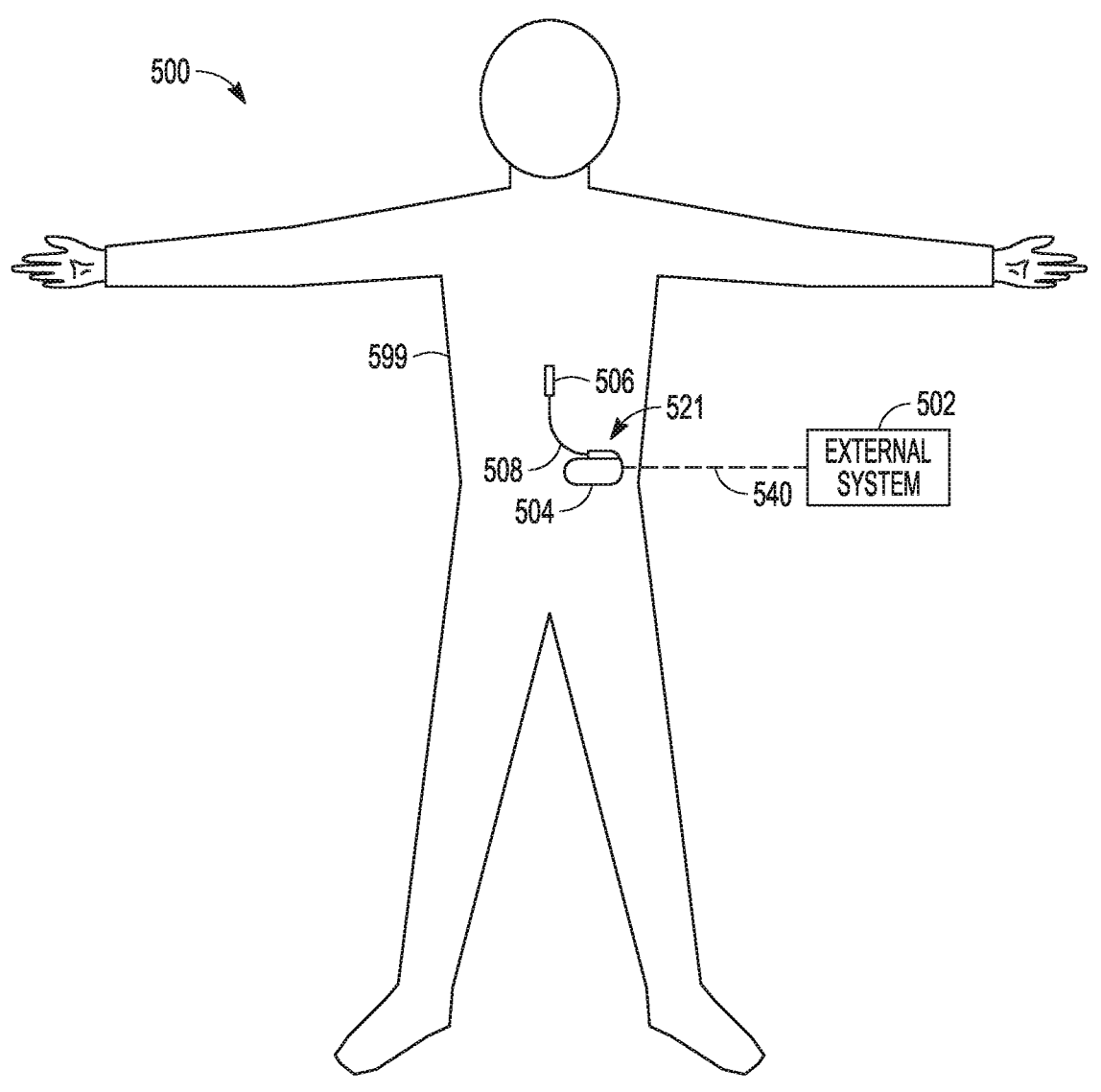
FIG. 5 illustrates an embodiment of an IPG and an implantable lead system, such as the IPG and lead system of FIG. 4, arranged to provide neurostimulation to a patient.

FIG. 5 illustrates an implantable neurostimulation system 500 and portions of an environment in which system 500 may be used. System 500 includes an implantable system 521, an external system 502, and a telemetry link 540 providing for wireless communication between implantable system 521 and external system 502. Implantable system 521 is illustrated in FIG. 5 as being implanted in the patient's body 599.

Implantable system 521 includes an implantable stimulator (also referred to as an implantable pulse generator, or IPG) 504, a lead system 508, and electrodes 506, which represent an example of stimulation device 204, lead system 208, and electrodes 206, respectively. External system 502 represents an example of programming device 302. In various embodiments, external system 502 includes one or more external (non-implantable) devices each allowing the user and/or the patient to communicate with implantable system 521. In some embodiments, external 502 includes a programming device intended for the user to initialize and adjust settings for implantable stimulator 504 and a remote control device intended for use by the patient. For example, the remote control device may allow the patient to turn implantable stimulator 504 on and off and/or adjust certain patient-programmable parameters of the plurality of stimulation parameters.

The sizes and sharps of the elements of implantable system 521 and their location in body 599 are illustrated by way of example and not by way of restriction. An implantable system is discussed as a specific application of the programming according to various embodiments of the present subject matter. In various embodiments, the present subject matter may be applied in programming any type of stimulation device that uses electrical pulses as stimuli, regarding less of stimulation targets in the patient's body and whether the stimulation device is implantable.

Returning to FIG. 4, the IPG 404 can include a hermetically-sealed IPG case 422 to house the electronic circuitry of IPG 404. IPG 404 can include an electrode 426 formed on IPG case 422. IPG 404 can include an IPG header 424 for coupling the proximal ends of leads 408A and 408B. IPG header 424 may optionally also include an electrode 428. Electrodes 426 and/or 428 represent embodiments of electrode(s) 207 and may each be referred to as a reference electrode. Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of the same lead (lead 408A or lead 408B). Neurostimulation energy can be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 6:
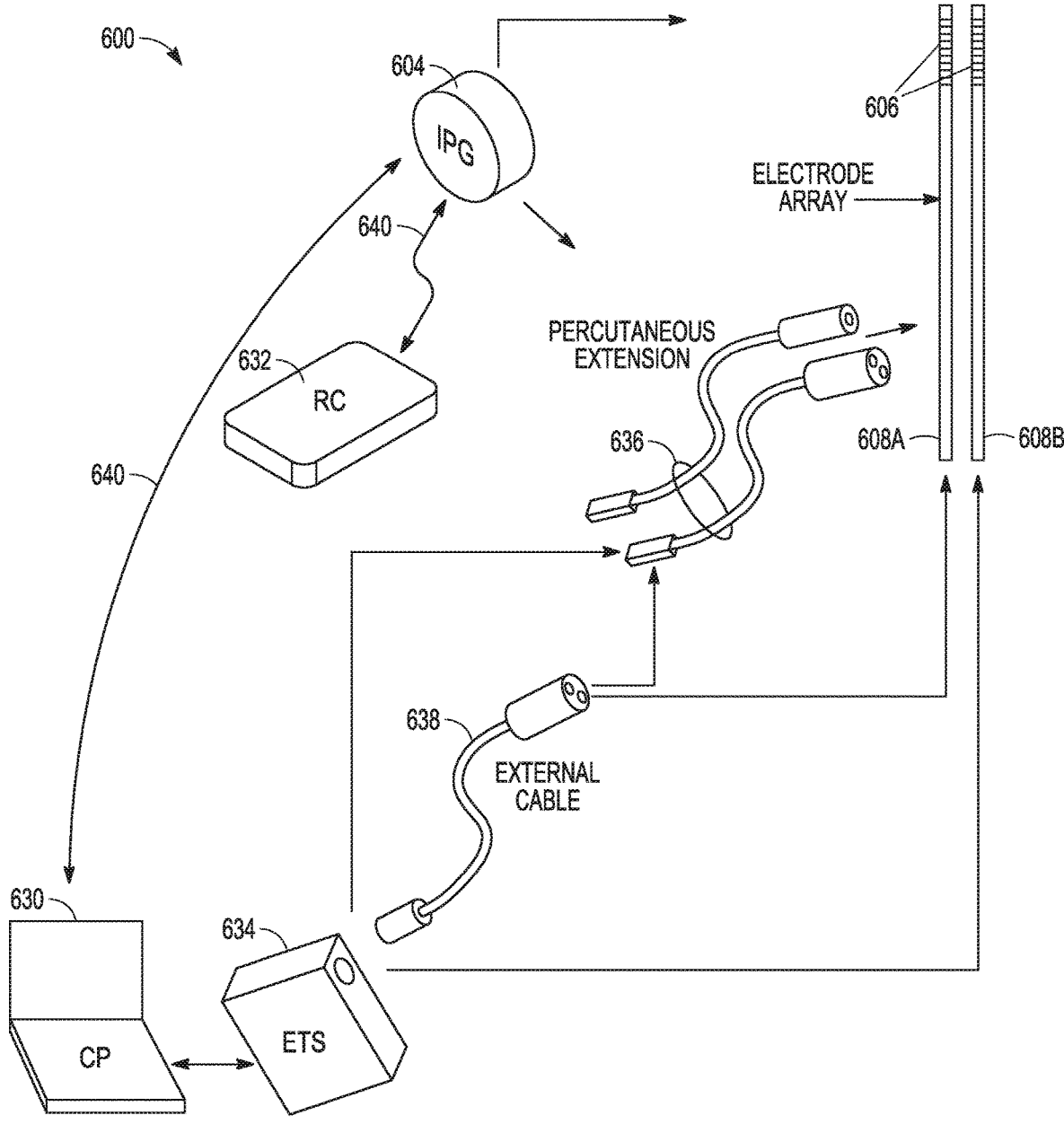
FIG. 6 illustrates an embodiment of portions of a neurostimulation system.

FIG. 6 illustrates an embodiment of portions of a neurostimulation system 600. System 600 includes an IPG 604, implantable neurostimulation leads 608A and 608B, an external remote controller (RC) 632, a clinician's programmer (CP) 630, and an external trial stimulator (ETS, also referred to as external trial modulator, ETM) 634. IPG 404 may be electrically coupled to leads 608A and 608B directly or through percutaneous extension leads 636. ETS 634 may be electrically connectable to leads 608A and 608B via one or both of percutaneous extension leads 636 and/or external cable 638. System 600 represents an example of system 100, with IPG 604 representing an embodiment of stimulation device 104, electrodes 606 of leads 608A and 608B representing electrodes 106, and CP 630, RC 632, and ETS 634 collectively representing programming device 102.

ETS 634 may be standalone or incorporated into CP 630. ETS 634 may have similar pulse generation circuitry as IPG 604 to deliver neurostimulation energy according to specified modulation parameters as discussed above. ETS 634 is an external device that is typically used as a preliminary stimulator after leads 408A and 408B have been implanted and used prior to stimulation with IPG 604 to test the patient's responsiveness to the stimulation that is to be provided by IPG 604. Because ETS 634 is external it may be more easily configurable than IPG 604.

CP 630 can configure the neurostimulation provided by ETS 634. If ETS 634 is not integrated into CP 630, CP 630 may communicate with ETS 634 using a wired connection (e.g., over a USB link) or by wireless telemetry using a wireless communications link 640. CP 630 also communicates with IPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of r=λ/2π, where λ is the wavelength of the transmitted electromagnetic energy.

In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link.

CP 630 can be used to set modulation parameters for the neurostimulation after IPG 604 has been implanted. This allows the neurostimulation to be tuned if the requirements for the neurostimulation change after implantation. CP 630 can also upload information from IPG 604.

RC 632 also communicates with IPG 604 using a wireless link 340. RC 632 may be a communication device used by the user or given to the patient. RC 632 may have reduced programming capability compared to CP 630. This allows the user or patient to alter the neurostimulation therapy but does not allow the patient full control over the therapy. For example, the patient may be able to increase the amplitude of neurostimulation pulses or change the time that a pre-programmed stimulation pulse train is applied. RC 632 may be programmed by CP 630. CP 630 may communicate with the RC 632 using a wired or wireless communications link. In some embodiments, CP 630 can program RC 632 when remotely located from RC 632.

Figure 7:
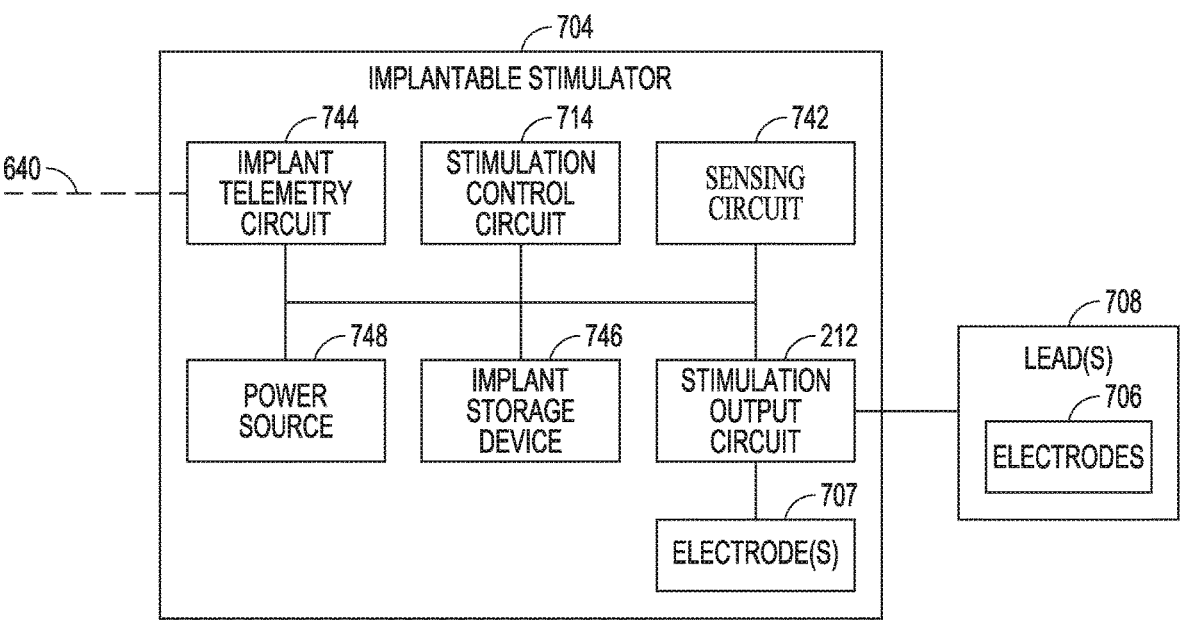
FIG. 7 illustrates an embodiment of an implantable stimulator and one or more leads of an implantable neurostimulation system, such as the implantable neurostimulation system of FIG. 6.

FIG. 7 illustrates an embodiment of implantable stimulator 704 and one or more leads 708 of an implantable neurostimulation system, such as implantable system 600. Implantable stimulator 704 represents an example of stimulation device 104 or 204 and may be implemented, for example, as IPG 604. Lead(s) 708 represents an example of lead system 208 and may be implemented, for example, as implantable leads 608A and 608B. Lead(s) 708 includes electrodes 706, which represents an example of electrodes 106 or 206 and may be implemented as electrodes 606.

Implantable stimulator 704 may include a sensing circuit 742 that provides the stimulator with a sensing capability, stimulation output circuit 212, a stimulation control circuit 714, an implant storage device 746, an implant telemetry circuit 744, a power source 748, and one or more electrodes 707. Sensing circuit 742 can one or more physiological signals for purposes of patient monitoring and/or feedback control of the neurostimulation. In various embodiments, sensing circuit 742 can sense one or more ESG signals using electrodes placed over or under the dura of the spinal cord, such as electrodes 706 (which can include epidural and/or intradural electrodes). In addition to one or more ESG signals, examples of the one or more physiological signals include neural and other signals each indicative of a condition of the patient that is treated by the neurostimulation and/or a response of the patient to the delivery of the neurostimulation. Stimulation output circuit 212 is electrically connected to electrodes 706 through one or more leads 708 as well as electrodes 707 and delivers each of the neurostimulation pulses through a set of electrodes selected from electrodes 706 and electrode(s) 707. Stimulation control circuit 714 represents an example of stimulation control circuit 214 and controls the delivery of the neurostimulation pulses using the plurality of stimulation parameters specifying the pattern of neurostimulation pulses. In one embodiment, stimulation control circuit 714 controls the delivery of the neurostimulation pulses using the one or more sensed physiological signals. Implant telemetry circuit 744 provides implantable stimulator 704 with wireless communication with another device such as CP 630 and RC 632, including receiving values of the plurality of stimulation parameters from the other device. Implant storage device 746 can store one or more neurostimulation programs and values of the plurality of stimulation parameters for each of the one or more neurostimulation programs. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 may also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4.

In one embodiment, implantable stimulator 704 is used as a master database. A patient implanted with implantable stimulator 704 (such as may be implemented as IPG 604) may therefore carny patient information needed for his or her medical care when such information is otherwise unavailable. Implant storage device 746 is configured to store such patient information. For example, the patient may be given a new RC 632 and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640 and allow for any necessary adjustment of the operation of implantable stimulator 704 based on the retrieved patient information. In various embodiments, the patient information to be stored in implant storage device 746 may include, for example, positions of lead(s) 708 and electrodes 706 relative to the patient's anatomy (transformation for fusing computerized tomogram (CT) of postoperative lead placement to magnetic resonance imaging (MRI) of the brain), clinical effect map data, objective measurements using quantitative assessments of symptoms (for example using micro-electrode recording, accelerometers, and/or other sensors), and/or any other information considered important or useful for providing adequate care for the patient. In various embodiments, the patient information to be stored in implant storage device 746 may include data transmitted to implantable stimulator 704 for storage as part of the patient information and data acquired by implantable stimulator 704, such as by using sensing circuit 742.

In various embodiments, sensing circuit 742 (if included), stimulation output circuit 212, stimulation control circuit 714, implant telemetry circuit 744, implant storage device 746, and power source 748 are encapsulated in a hermetically sealed implantable housing or case, and electrode(s) 707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
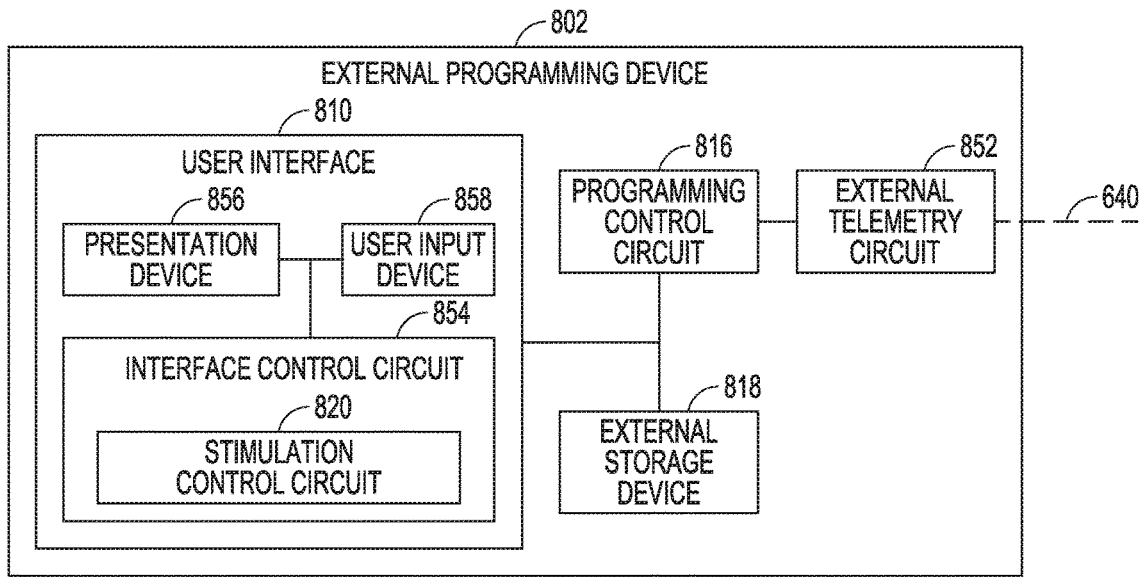
FIG. 8 illustrates an embodiment of an external programming device of an implantable neurostimulation system, such as the implantable neurostimulation system of FIG. 6.

FIG. 8 illustrates an embodiment of an external programming device 802 of an implantable neurostimulation system, such as system 600. External programming device 802 represents an example of programming device 102 or 302, and may be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). This can allow for patient mobility during programming and assessment when needed. For example, wireless communication link 640 can include at least a far-field telemetry link that allows for communications between external programming device 802 and implantable stimulator 704 over a relative long distance, such as up to about 20 meters. External telemetry circuit 852 and implant telemetry circuit 744 each include an antenna and RF circuitry configured to support such wireless telemetry.

External storage device 818 stores one or more stimulation waveforms for delivery during a neurostimulation therapy session, such as a SCS therapy session, as well as various parameters and building blocks for defining one or more waveforms. The one or more stimulation waveforms may each be associated with one or more stimulation fields and represent a pattern of neurostimulation pulses to be delivered to the one or more stimulation field during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 may include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through which a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. Such definition of the current distribution may be referred to as "fractionalization" in this document. In another embodiment, the current distribution is defined by assigning an amplitude value to each electrode of the set of electrodes. For example, the set of electrodes may include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steering a stimulation locus, and stimulation changes on multiple contacts simultaneously to move the locus while holding the stimulation amount constant. Control and displaying the total current through each electrode in terms of absolute values (e.g., mA) allows precise dosing of current through each specific electrode. It is suited for changing the current one contact at a time (and allows the user to do so) to shape the stimulation like a piece of clay (pushing/pulling one spot at a time).

Programming control circuit 816 represents an example of programming control circuit 316 and generates the plurality of stimulation parameters, which is to be transmitted to implantable stimulator 704, based on a specified neuro-stimulation program (e.g., the pattern of neurostimulation pulses as represented by one or more stimulation waveforms and one or more stimulation fields, or at least certain aspects of the pattern). The neurostimulation program may be created and/or adjusted by the user using user interface 810 and stored in external storage device 818. In various embodiments, programming control circuit 816 can check values of the plurality of stimulation parameters against safety rules to limit these values within constraints of the safety rules. In one embodiment, the safety rules are heuristic rules.

User interface 810 represents an example of user interface 310 and allows the user to define the pattern of neurostimulation pulses and perform various other monitoring and programming tasks. User interface 810 includes a display screen 856, a user input device 858, and an interface control circuit 854. Display screen 856 may include any type of interactive or non-interactive screens, and user input device 858 may include any type of user input devices that supports the various functions discussed in this document, such as touchscreen, keyboard, keypad, touchpad, trackball, joy-stick, and mouse. In one embodiment, user interface 810 includes a GUI. The GUI may also allow the user to perform any functions discussed in this document where graphical presentation and/or editing are suitable as may be appreciated by those skilled in the art.

Interface control circuit 854 controls the operation of user interface 810 including responding to various inputs received by user input device 858 and defining the one or more stimulation waveforms. Interface control circuit 854 includes a stimulation control circuit 820.

In various embodiments, external programming device 802 can have operation modes including a composition mode and a real-time programming mode. Under the composition mode (also known as the pulse pattern composition mode), user interface 810 is activated, while programming control circuit 816 is inactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms and transmits the plurality of stimulation parameters with the updated values to implantable stimulator 704.

Stimulation control circuit 820 represents an example of stimulation control circuit 320 and can be configured to detect lead migration (e.g., displacement of lead(s) 708 in tissue after implantation in the patient) and to adjust system settings related to the delivery of the neurostimulation when needed (e.g., when the detected lead migration exceeds a tolerance threshold). In various embodiments, stimulation control circuit 820 can be configured to detect lead migration, including measuring the amount of migration and assessing reliability of the measurements using various techniques, and to respond to the detected lead migration by adjusting the delivery of the neurostimulation and/or informing the patient and/or the user, among other things, as discussed below in this document.

Figure 9:
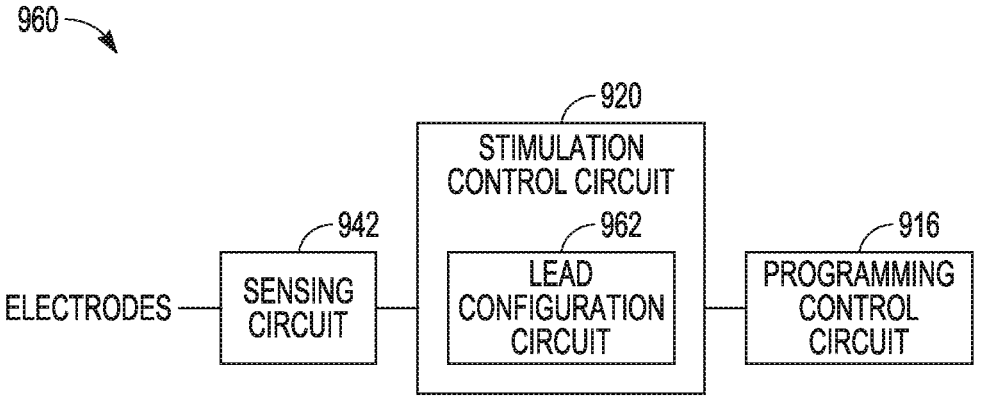
FIG. 9 illustrates an embodiment of a system for detecting lead migration and adjusting neurostimulation based on the detection.

FIG. 9 illustrates an embodiment of a system 960 for detecting lead migration and adjusting neurostimulation based on the detection. In one embodiment, system 960 is part of a system for delivering neurostimulation to a patient through a plurality of electrodes using first and second leads each including one or more electrodes of the plurality of electrodes. For example, system 960 can be implemented in system 100, including but not limited to the various examples of the system (systems 500 and 600) and components of the system as discussed in this document. The first and second leads can be selected from leads 708, which can include two or more leads in this embodiment. System 960 includes a programming control circuit 916, a sensing circuit 942, and a stimulation control circuit 920.

Programming control circuit 916 represents an example of programming control circuit 816 and can be configured to generate stimulation parameters controlling delivery of the neurostimulation according to one or more stimulation waveforms and one or more stimulation fields. The one or more stimulation fields each specify a distribution of a stimulation energy over the plurality of electrodes. Sensing circuit 942 represents an example of sensing circuit 842 and can be configured to sense signals using sensing electrodes selected from the plurality of electrodes. Stimulation control circuit 920 represents an example of stimulation control circuit 820 and can be configured to determine the one or more stimulation waveforms and the one or more stimulation fields based on a lead configuration including positions of the plurality of electrodes. Stimulation control circuit 920 includes a lead configuration circuit 962. Lead configuration circuit 962 can be configured to determine a first electrode of the first lead and a second electrode of the second lead, receive a first signal sensed using the first electrode and a second signal sensed using the second electrode, detect a first signal feature from the first signal and a second signal feature from the second signal, determine a feature delay being a time interval between the detected first and second signal features, and determine a need for adjusting the lead configuration using the feature delay. The first and second signal features can be morphological features of the first and second signals, respectively, that are associated with a response of the patient to the neurostimulation.

Figure 10A:
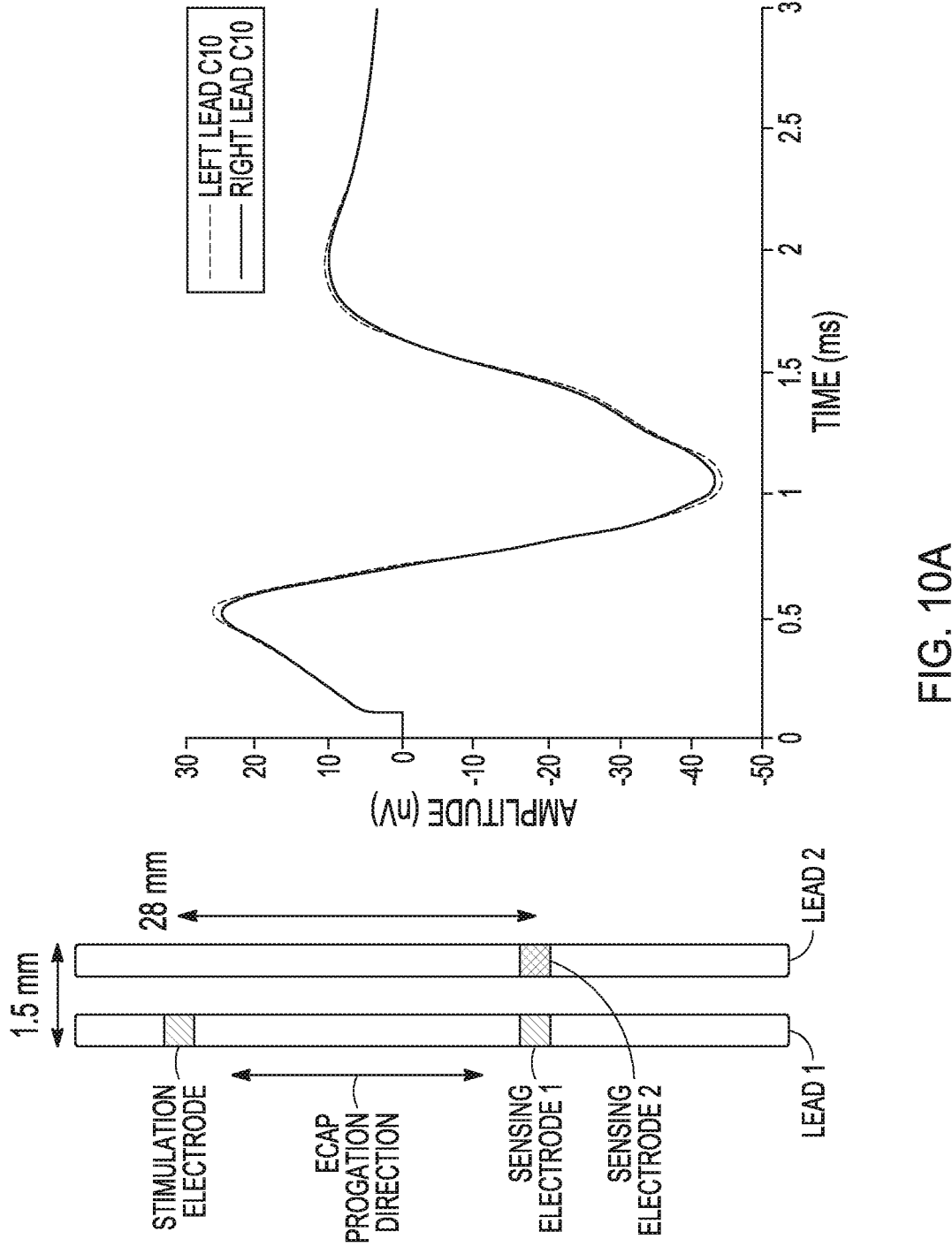
FIGS. 10A-B illustrate examples of sensed neural response signals including signal features indicating lead migration, with FIG. 10A showing an example with two parallel leads aligned and FIG. 10B showing an example of with the two parallel leads having an offset distance resulting from lead migration.
Figure 10B:
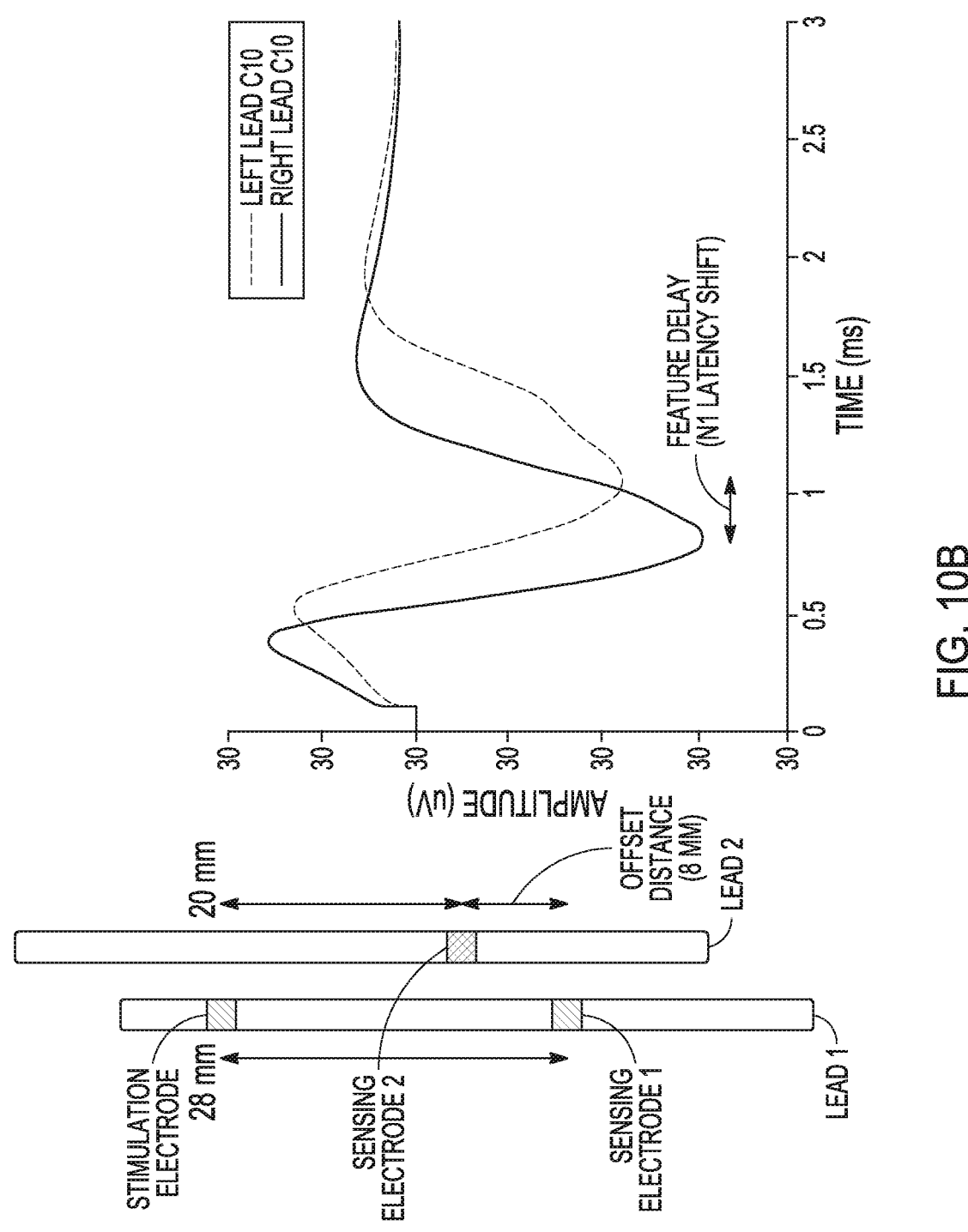

FIGS. 10A-B illustrate examples of the signals to be sensed by sensing circuit 942. The signals include signal features indicating lead migration. FIG. 10A shows an example with two parallel leads aligned, and FIG. 10B shows an example of with the two parallel leads having an offset distance resulting from lead migration. The first lead ("LEAD 1" in FIGS. 10A-B) and the second lead ("LEAD 2" in FIGS. 10A-B) are two leads connected to system 960. The first and second leads are part of a system including two or more leads that include a plurality of electrodes. The first and second leads can each include one or more electrodes of the plurality of electrodes. The first lead can include one or more first electrodes of the plurality of electrodes. The second lead can include one or more second electrodes of the plurality of electrodes. In this document, a "lead configuration" includes information identifying positions of the electrodes and can include one or more offset distances quantitatively indicative of a position of the first lead relative to the second lead. The one or more offset distances each represent a distance between a first electrode and a second electrode in one direction (e.g., along the longitudinal axes of the leads when the first and second leads are placed in parallel, such as in rostrocaudal direction when the first and second lead are placed in parallel for SCS, as illustrated in FIGS. 10A-B). While two leads are illustrated in each of FIGS. 4, 6, 10, and 12-16 and discussed as examples, the present subject matter can be applied to systems each including any number of leads. For example, the offset distance can be determined between electrodes of any two leads of a system including two or more leads.

Many nerve cells produce low-level electrical signals, called action potentials, that form electrical activity patterns and, in many instances, can have an additive effect producing a magnified neural response. An example is the evoked compound action potential (ECAP), which is evoked by a stimulation such as a neurostimulation pulse and results from many neural cells firing simultaneously or close in time.

One example of the signals sensed by sensing circuit 942 include neural signals including evoked compound action potentials (ECAPs) that propagate from stimulation site can be sensed at a recording site. One or more features can be detected from the sensed ECAPS, and the delay between a stimulus and a detected feature can be detected as an indication for the distance between the stimulation site and the recording site. For example, times at which an ECAP arrives at recording sites on parallel leads with a common geometric reference point (e.g., the stimulation site) can be compared with each other to derive offsets (in the direction of ECAP propagation) between the leads. FIGS. 10A-B illustrate an example of ECAP model predictions of effect of positional shift of two leads placed parallel to the direction of the ECAP propagation (e.g., the rostrocaudal direction when the two leads are placed for SCS). FIG. 10A shows the ECAP signals sensed at the recording electrode of each lead of two parallel leads with their recording electrodes aligned (i.e., zero offset) in the direction of the ECAP propagation. FIG. 10B shows the ECAP signals sensed at the recording electrode of each lead of two parallel leads with their recording electrodes offset by 8 mm resulting from positional shift of parallel leads in the direction of the ECAP propagation. Positional shift of lead parallel to sensed neurite propagation (e.g., in the rostrocaudal direction) results in shift between corresponding features in the ECAP signals detected from electrodes of different leads, even if the electrodes are also offset in the perpendicular (e.g., mediolateral) direction. While a time offset between features detected from the sensed ECAP signals can be used to indicate a positional shift between two parallel leads, as illustrated in FIGS. 10A-B, determination of exact direction of the positional shift may require additional information such as morphology of the detected features.

Experiments have shown that for SCS, the ECAP signals recorded by the sensing electrodes can be mapped with the positions of the sensing electrodes determined relative to intervertebral discs. During implantation of a lead, original position of an electrode can be related to an anatomical landmark with respect to the spinal cord (e.g., an intervertebral disc), and an ECAP signal can be sensed using the electrode in its original position and stored as a template ECAP signal for that electrode. After the implantation, the ECAP signal sensed using that electrode can be compared to the stored template ECAP signal to determine whether the lead has migrated based on whether there is a difference between the sensed ECAP signal and the stored template ECAP signal. If there is a lead migration, the new position of the electrode can be determined using the time and/or morphological difference(s) between the sensed ECAP signal and the stored template ECAP signal and the location of the anatomical landmark related to the original position of the electrode. This approach allows for determination of lead migration when only a single lead is placed and can be applied for either a percutaneous lead or a paddle lead. The attenuation of the ECAP signal along the distance from the stimulation site can also be modeled mathematically. This approach allows for verification of the offset distance determined using the offset time (FIGS. 10A-B) by determining the offset distance using amplitude of the ECAP signal.

Figure 11:
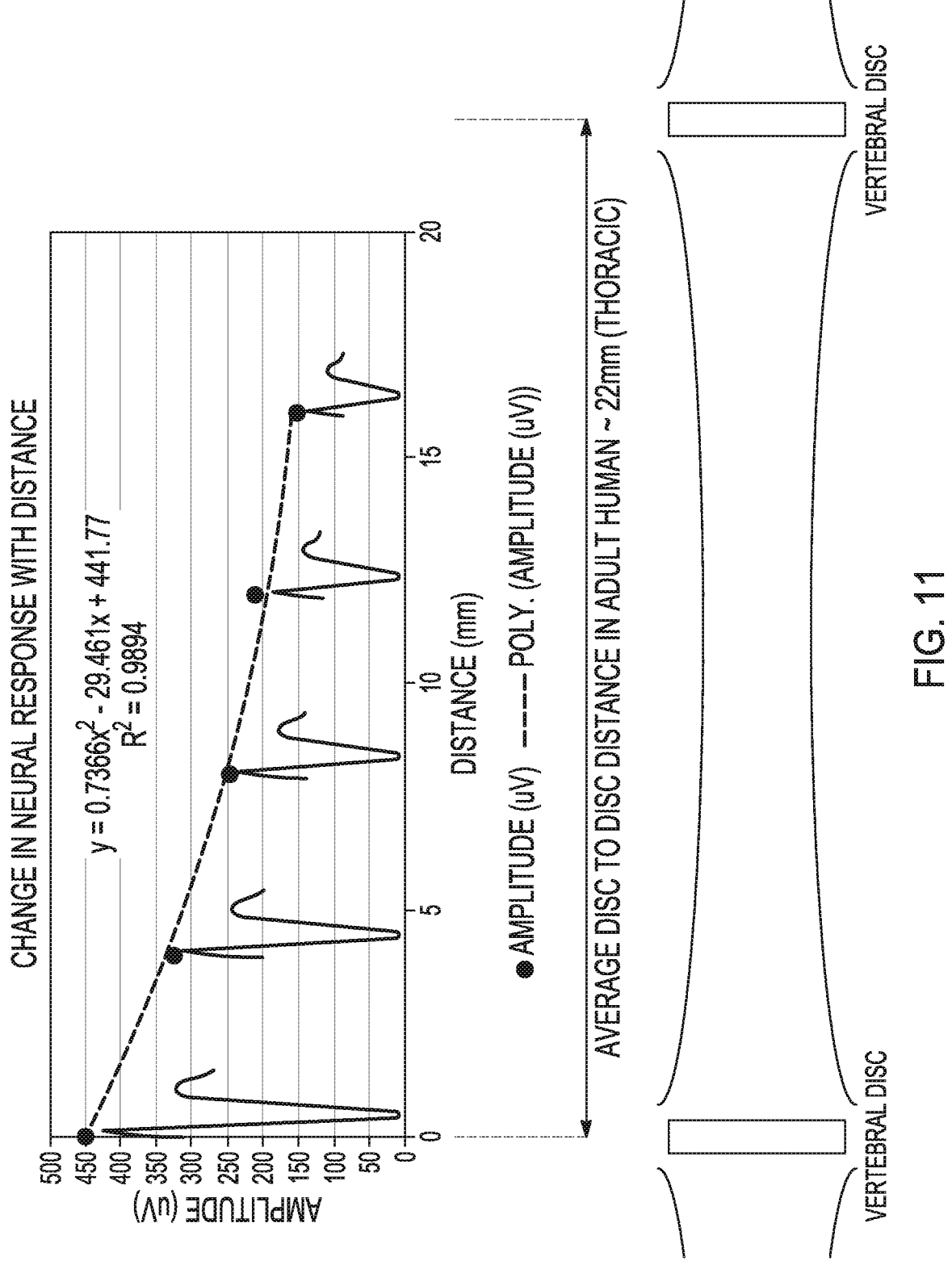
FIG. 11 illustrates an example of amplitude of a sensed neural response signal that changes with distance.

FIG. 11 illustrates an example of amplitude of a sensed neural response signal that changes with distance. FIG. 11 shows ECAP signals at various distances from the stimulation site that are produced using mathematical models and can be used as template ECAP signals for determining lead migration. When two or more leads are placed, a matrix of ECAP spatial amplitudes can be created, and a spatial model can be associated to the matrix based on the spatial grid position. A change in the ECAP amplitude that exceeds a margin of acceptable error can be used to detect a lead migration. The amount of the change can be used to indicate an amount of the migration and, with additional information such as signal morphology, to estimate a direction of the lead migration. The amount and direction of lead migration can be used to adjust neurostimulation therapy settings to maintain efficacy. In this document, the "lead configuration" can include the one or more offset distances each quantitatively indicative of the position of the first lead relative to the second lead, one or more offset distances each quantitatively indicative of movement of a lead related to an anatomical reference point (e.g., a vertebral disc), and/or one or more other parameters allowing for identifying the position of a lead.

In various embodiments, lead configuration circuit 962 can determine lead configurations, including a "locked-in" lead configuration, using the sensed signals, and stimulation control circuit 920 can determine the one or more stimulation waveforms and the one or more stimulation fields based on the locked-in lead configuration. In this document, the "locked-in" lead configuration includes a lead configuration that is saved for use in determining the one or more stimulation waveforms and one or more stimulation fields, which in turn are used to generate the stimulation parameters controlling the delivery of neurostimulation. Various embodiments of lead configuration circuit 962 are further discussed below.

Figure 12:
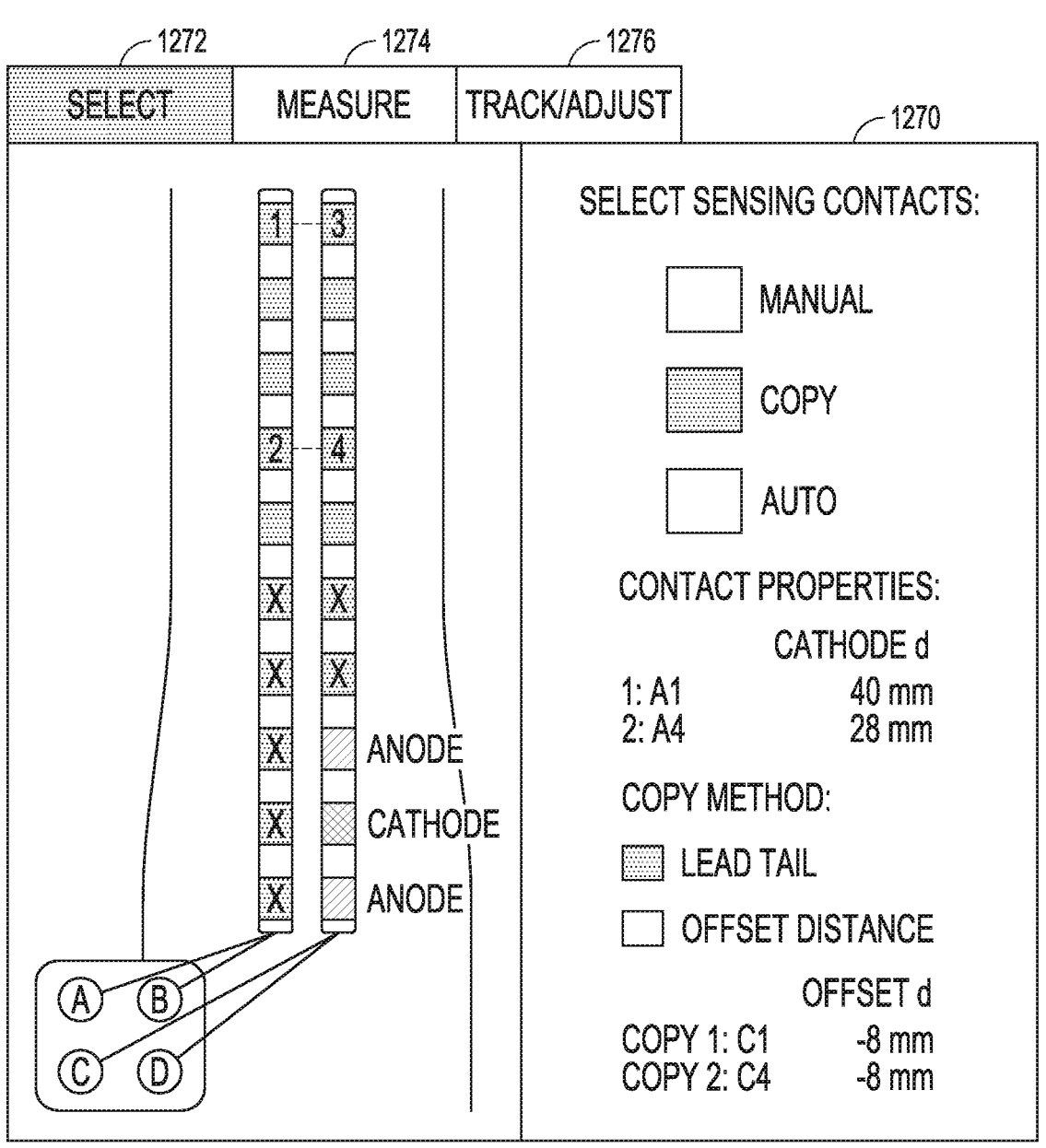
FIG. 12 illustrates an embodiment of a portion of a user interface screen allowing for electrode selection during an initial calibration for offset distance measurements.

FIG. 12 illustrates an embodiment of a portion of a user interface screen 1270 allowing for electrode selection during an initial calibration for offset distance measurements. User interface screen 1270 represents an example of presentation device 856 and a select tab 1272, a measure tab 1274, and a track/adjust tab 1276. Selection of one of select tab 1272, measure tab 1274, and track/adjust tab 1276 (e.g., using a user input device such as user input device 854) opens a respective field (or window) on screen 1270.

Detection of lead migration can start with an initial calibration that establishes an initial lead configuration. The initial calibration can be performed after the user places one or more leads in the patient with positioning aided by fluoroscopy and connects the one or more leads to a stimulation device.

When select tab 1272 is selected, a selection field is displayed on screen 1270, as illustrated in FIG. 12. Lead configuration circuit 962 can select electrodes for the initial calibration. In various embodiments, lead configuration circuit 962 can select one or more electrodes from each lead of the one or more leads placed in the patient. In the illustrated embodiment, the pair of first and second leads (as discussed above) are placed in the patient, and their graphical representation is displayed in the selection field on screen 1270. Lead configuration circuit 962 can select one or more pairs of first and second electrodes from the pair of the first and second leads. Each pair of the one or more pairs of electrodes includes a first electrode of one or more first electrodes of the first lead and a second electrode of one or more second electrodes of the second lead. Lead configuration circuit 962 can allow for multiple electrode selection options, such as:

a "manual" selection option: the user manually selects the one or more electrodes, and the system presents a warning message if the selection is inappropriate (e.g., insufficient electrodes selected, such as only electrodes on one lead are selected when two or more leads are placed);

a "copy" selection option: the user manually selects one or more electrodes on one lead, and the system automatically copies the selection onto another lead, the copy option can include:

a "lead tail" copy option: the system automatically selects "analogous" electrodes on the other lead; and/or an "offset distance" copy option: the system automatically selects longitudinally (e.g., rostro-caudally in case of leads for SCS) offset electrodes based on user-specified distance (e.g., if two lead are aligned and 0 mm offset is specified, the selection will be the same as the "lead tail" option, i.e., "analogous" electrodes are selected); and/or an "auto" selection option: the system automatically selects the one or more electrodes based on specified distances from a calibration stimulation electrode (e.g., a cathode through which stimulation pulses are delivered for the initial calibration). Example: selectable electrodes at minimum and maximum distances (electrodes too close to the stimulation site may not be selectable). These settings will likely be pre-loaded (e.g., pick one pair at least 16 mm away, another pair at most 36 mm away, and pairs must be separated by 12-20 mm).

Lead configuration circuit 962 can present pertinent information to the user (e.g., the distance of each selected electrode from the calibration stimulation cathode, and the offset distance between electrodes of each selected pair of electrodes) in the selection field on screen 1270. The "Offset Approximation" shown in FIG. 12 is the offset distance, which is an approximation of the offset distance calculated based on the corresponding feature delay.

Figure 13:
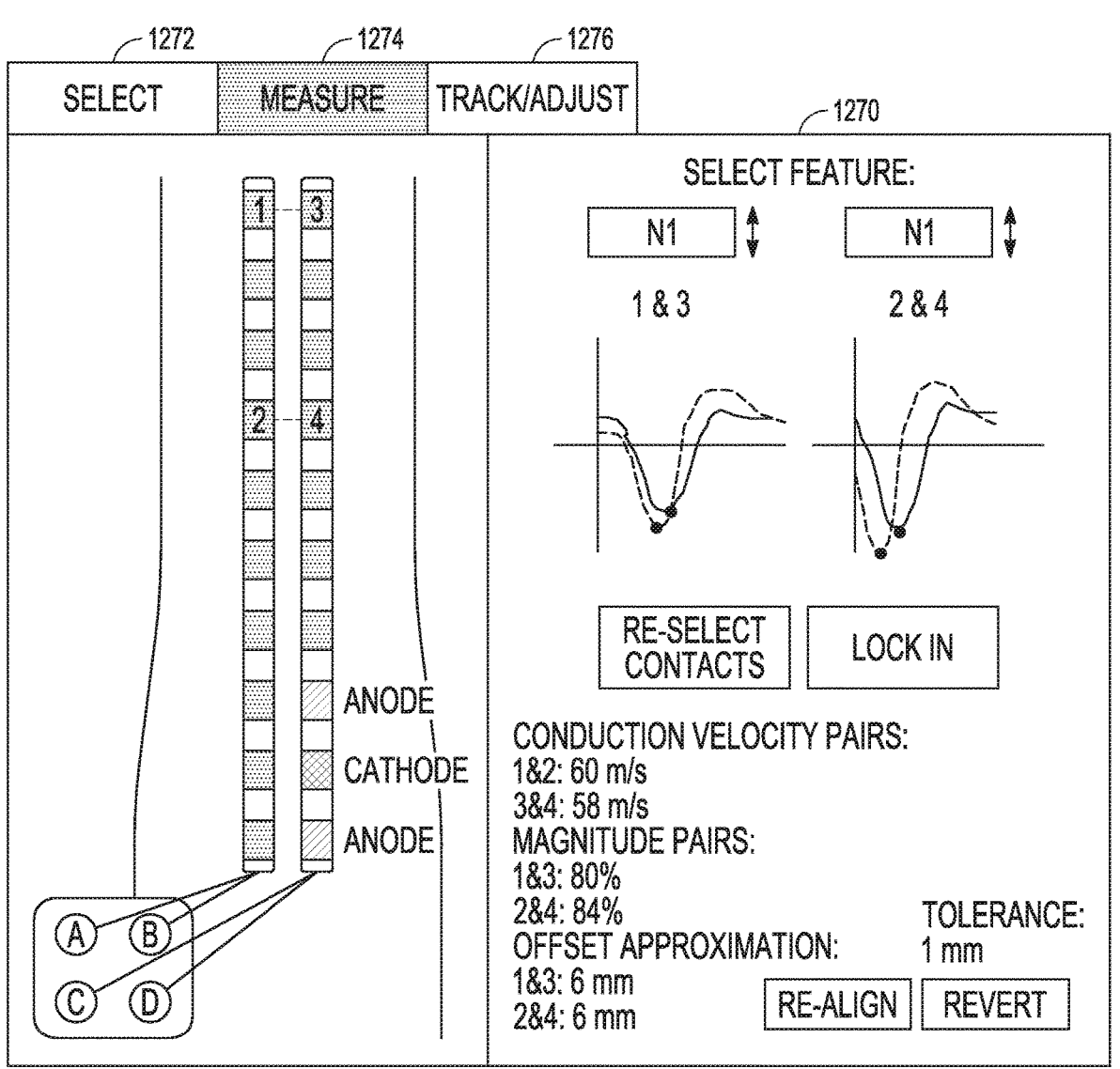
FIG. 13 illustrates an embodiment of a portion of the user interface screen allowing for measurements during the initial calibration for offset distance measurements.

FIG. 13 illustrates an embodiment of a portion of user interface screen 1270 allowing for measurements during the initial calibration for offset distance measurements. After the electrodes are selected, lead configuration circuit 962 can receive signals each sensed using an electrode of the selected electrodes. The signals can include neural signals each including ECAPs, as discussed above. When measure tab 1274 is selected, a measurement field (or window) is displayed on screen 1270, as illustrated in FIG. 13. Lead configuration circuit 962 can display the sensed signals in the measurement field on screen 1270.

Lead configuration circuit 962 can select a signal feature for the initial calibration. The signal feature is associated with a neural response to a stimulus of the neurostimulation. In various embodiments, lead configuration circuit 962 can select the signal feature by receiving a selection of the user. The user can make the selection upon observing the sensed signals displayed in the measurement field on screen 1270. Examples of signal features in a neural signal including ECAPs can include:

N1 (where N1 is the first negative peak in an evoked response that is correlated to the response of faster fibers such as $\Delta\beta$ fibers and myelinated fibers);

P2 (where P2 is the second positive peak in the evoked response that is correlated with response of slower fibers);

N2 (where N2 is the second negative peak in the evoked response); and

P3 (where P3 is the third positive peak in the evoked response, which are correlated with responses of even slower fibers (e.g., $A\delta$ fibers).

In various embodiments, lead configuration circuit 962 can measure a time offset between the corresponding features associated with each pair of electrodes in different leads and can calculate an offset distance between the pair of electrodes based on the time offset. In various embodiments, lead configuration circuit 962 allows two or more features to be selected for confirmatory purposes (e.g., by comparing offset distances calculated based on different signal features).

After the signal feature is selected, lead configuration circuit 962 can perform measurements automatically for the initial calibration. The measurements can determine at least a temporal relationship between the signal features in the signals sensed by each pair of first and second electrodes of the selected one or more pairs of first and second electrodes. In one embodiment, lead configuration circuit 962 performs the measurements automatically in response to a measurement command from the user. For example, after selecting the electrodes and the signal feature, the user clicks a "Measure" button displayed in the measurement field on screen 1270. In response, lead configuration circuit 962 automatically determines a position of each electrode of the selected electrodes relative to another electrode of the selected electrodes or relative to an anatomical reference point. This position can be measured by an offset distance between a pair of electrodes of the selected one or more pairs of electrodes. In various embodiments, lead configuration circuit 962 automatically determines an offset distance for each pair of electrodes of the selected one or more pairs of electrodes (two pairs of electrodes are shown in FIG. 13 for illustrative purposes).

In one embodiment, the measurements allow for determination of an offset distance between the pair of first and second electrodes selected from the respective first and second leads. Lead configuration circuit 962 detects the selected signal feature from the signal sensed using each of the first and second electrodes, determines a conduction velocity using the signal features detected from the signals sensed using two electrodes selected from each lead, measures a feature delay being a time interval between the signal features detected from the signals sensed using the first and second electrodes, and determine the offset distance by multiplying the determined conduction velocity by the measured feature delay. In various embodiments, the conduction velocity can be determined by using the known distance between two electrodes and a feature delay measured for these two electrodes, where distance between the two electrodes can be determined from known lead geometry, measured from an x-ray image, and/or using a distance between the two electrodes estimated using an electronically generated lead scan (e.g., using stimulation to induce electrical field in tissue to measure tissue properties related to propagation of action potentials independent of physiological response).

In one embodiment, lead configuration circuit 962 measures one or more morphological parameters associated with a morphological feature of the signal sensed using each electrode of the selected electrodes and determine an offset distance between the electrode and a reference position (e.g., an anatomical landmark such as a particular intervertebral disc). The one or more morphological parameters can include, but are not limited to, magnitude of the signal (e.g., as measured by amplitude of a signal feature) and width or duration of a signal feature. When multiple signals are sensed, the one or more morphological parameters can also include parameters measured between corresponding signal features of different signals, such as the time interval between a pair of corresponding signal features of signals sensed using two leads. The magnitude of the signal is specifically discussed in this document by way of example, but not by way of limitation, for illustrating use of the one or more morphological parameters in the present subject matter, including but not limited to the determination and/or verification of the offset distance. In various embodiment, using the one or more morphological parameters, such as the magnitude of the signal, allows for verification of the offset distance determined based on the feature delay. In various other embodiment, this allows for detecting lead migration by detecting a change of position of the electrode relative to a previous (e.g., initial) position of the electrode by comparing the magnitude measured at a current position to the magnitude measured at the previous position. In various embodiments, additional information such as change in morphological features of ECAP may be needed to indicate direction of lead migration.

Lead configuration circuit 962 can compare the determined offset distance to a specified tolerance. In various embodiments, the tolerance can be specified as an absolute value (referring to a fixed offset distance) or a relative value (referring to a previously determined offset distance, for example the offset distance determined during the initial calibration, which may or may not be zero). The specified tolerance can indicate a need for adjusting the locked-in lead configuration. Lead configuration circuit 962 can recommend a re-alignment option in response to the determined offset distance exceeding the specified tolerance. In one embodiment, in response to the recommendation not being accepted (e.g., the user chooses to continue with the existing locked-in configuration), lead configuration circuit 962 presents on screen 1270 a warning message. For example, the warning message can include: "Warning: Feature recordings suggest offset in leads inconsistent with 'locked-in' configuration. If you continue, automatic physiologically-based lead adjustment will not be available. Continue anyway?" Then, lead configuration circuit 962 allows the user to make adjustment manually.

Figure 14:
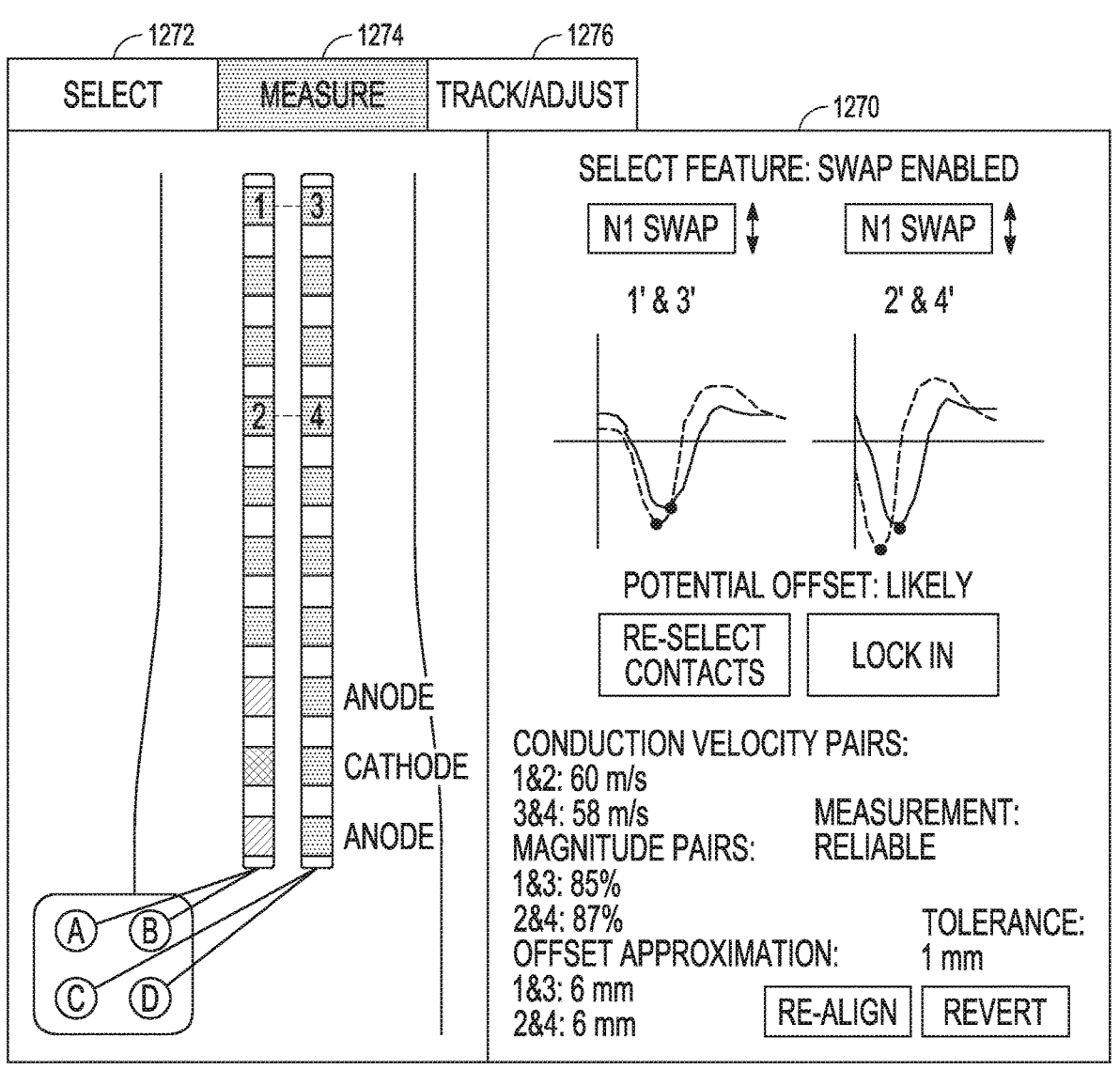
FIG. 14 illustrates an embodiment of a portion of the user interface screen allowing for reliability assessment during an initial calibration for offset distance measurements.

FIG. 14 illustrates an embodiment of a portion of user interface screen 1270 allowing for reliability assessment during the initial calibration for offset distance measurements. Lead configuration circuit 962 can perform an assessment of reliability of the measurements made during the initial calibration and display the result of the assessment in the measurement field of screen 1270. The result can be used to determine a need for reselecting electrodes and/or signal features for a more reliable measurement (e.g., with easier feature detection, larger measured values, and/or higher sensitivity of the measured values to lead displacement). In various embodiments, the reliability of the measurements can be assessed to ensure that the selection of electrodes provides for reliable approximation of the offset distance(s), ensure that the measurements of the feature delay(s) generate consistent results, and/or incorporate attenuation of the sensed signal into the approximation of the offset distance(s).

In various embodiments, lead configuration circuit 962 can produce a reliability metrics including multiple parameters indicative of the reliability of the measurements. Figures of merit and/or "stimulation swap" with recording electrodes can be used to determine parameters indicative of the reliability of the measurements such as:

Offset likelihood, which indicates likeliness of offset (i.e., lead migration that has actually occurred); and Measurement reliability, which indicates reliability of results of the measurements (as measured by consistency of the results).

Figures 15A, 15B, 15C:
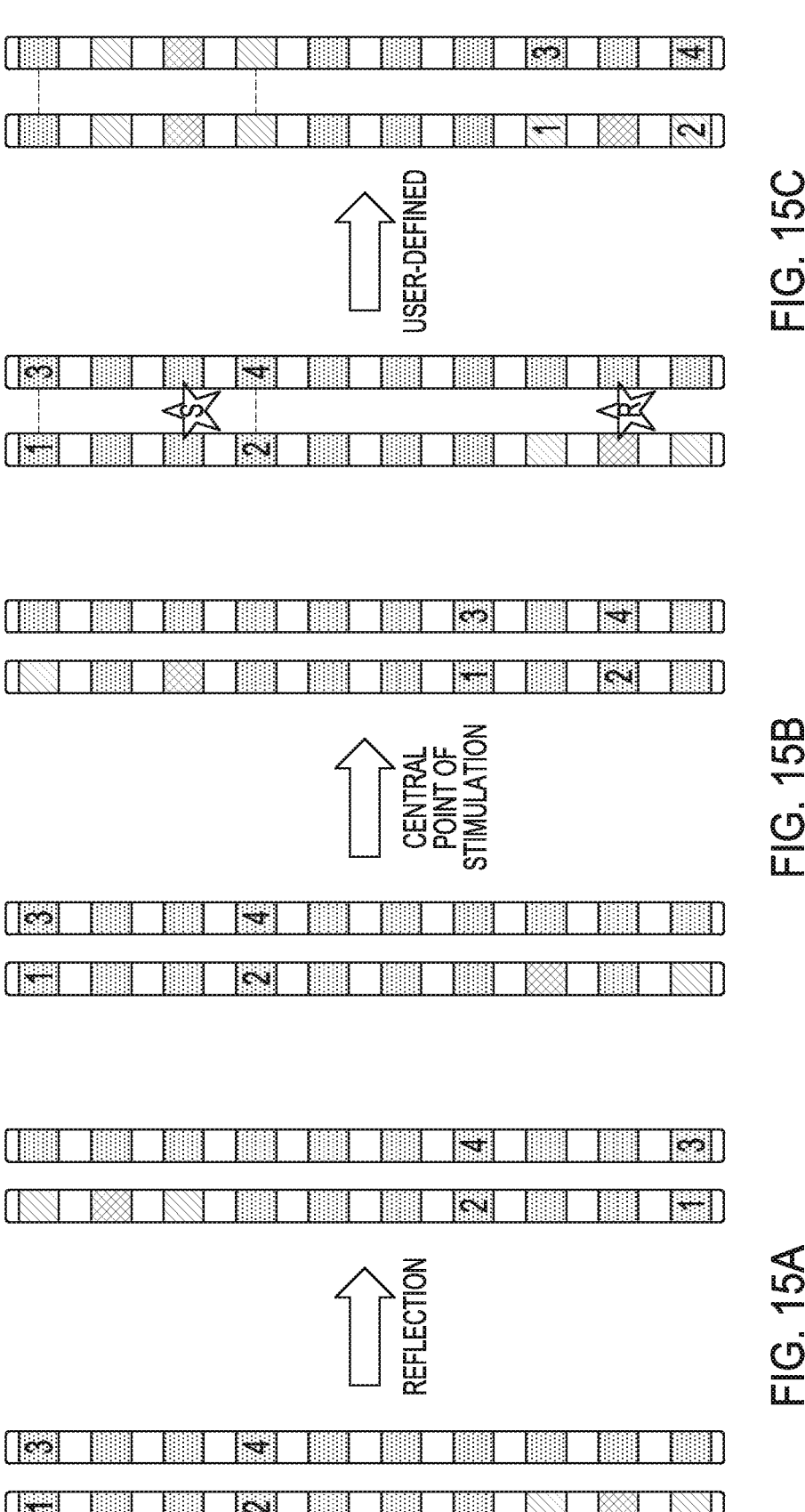
FIGS. 15A-C each illustrate an embodiment of stimulation swap used for the reliability assessment, with FIG. 15A illustrating a reflection swap, FIG. 15B illustrating a central point of stimulation swap, and FIG. 15C illustrating a user-defined swap.

FIGS. 15A-C each illustrate, by way of example, an embodiment of stimulation swap used for the reliability assessment. In each of FIGS. 15A-C, a pair of leads is shown with electrodes 1-4 labeled to indicate their positions before the stimulation swap (on the left) and after the stimulation swap (on the right). In FIG. 15A, the stimulation swap includes "reflecting" the stimulation geometry (the geometric arrangement of electrodes) across the midpoint of the lead. In FIG. 15B, the "central point of stimulation" (rather than the specific geometry) is swapped about a user- or device-defined symmetry point in an analogous matter. An auto-calculation algorithm then determines the final stimulation geometry. In FIG. 15C, the entire stimulation geometry is mirrored. In all these embodiments, the stimulation geometry can be "swapped" about a user-defined electrode rather than about a symmetric point or plane. In all these embodiments, the original (pre-swap) stimulating electrodes are set to be recording electrodes. Other embodiments of stimulation swap can also be applied as deemed appropriate or advantageous by those skilled in the art.

Table 1 lists examples of the parameters indicative of the reliability of the measurements.

TABLE 1

| Parameters indicative of offset likelihood and/or measurements reliability, where Δs is the feature delay. | | |
| --- | --- | --- |
| Parameters | Offset Likelihood? | Measurement reliability? |
| Δs between mediolateral measures | Yes | |
| Δs between mediolateral measures following rostrocaudal swap | | Yes |
| Δs between rostrocaudal measures | | Yes |
| Δs between rostrocaudal measures following rostrocaudal swap | Yes | Yes |
| Magnitude, attenuation of respective electrodes in different leads (e.g., 1 vs. 3 and or 2 vs. 4 in FIG. 14) | | Yes |

Examples of the parameters indicative of the offset likelihood include (based on ECAP features, confirmatory after swap, but can be stand-alone):

N1-N1 delay time differences;
N1-P2 width differences;
P2-P2 delay time differences;

presence of N2 and/or P3 between one or more pairs of
electrodes or leads (i.e., whether this can be replicated
by swapping stimulation); and potential mediolateral application: ratio of negative and
positive peak amplitudes.

Examples of the parameters indicative of measurement
reliability (e.g., consistency of results of the measurements,
with smaller changes indicate higher reliability) include
(after mediolateral or rostrocaudal swap):

conduction velocity of referential ECAP on different
electrodes or leads;

conduction velocity of differential ECAP on pairs of
electrodes on leads placed in parallel;

ECAP width on different electrodes or pairs of electrodes
contacts; and change in measured offset distances above after stimula-
tion swap.

In various embodiments, an offset metrics can include one or
more parameters indicative of the offset likelihood, a mea-
surement liability metrics can include one or more param-
eters indicative of measurement reliability. Values of the
offset metrics and measurement metrics to be presented to
the user can include:

digital (i.e., binary): the values can include "Keep" (or
equivalent) or "Change" (or equivalent) based on the
specific tolerances (e.g., "Keep" if the peak latency $\Delta s$
are below 0.04 ms and the conduction velocity differ-
ences are within sampling uncertainty of e.g., 10 m/s
after a swap; "Change" otherwise);

tiered (i.e., multiple levels): the values can include dif-
ferent levels of offset and measurement certainty based
on value ranges. For example, "Offset Likely" and
"Measurement Reliable" could be shown for metrics
above; offset can be otherwise classified as "Possible",
"Consider", "Unlikely" (or analogues) whereas mea-
surements can be classified as "Moderate", "Unclear",
"Unreliable" (or analogues) based on value ranges;
and/or analog (i.e., continuous): the values can be on a sliding
scale (e.g., green for good to red for bad over a color
gradient), the value of the metric itself, a modified scale
factor or score (e.g., rating on 0 to 100) and/or another
analog representation of the figure of metric could be
shown to the user.

Figure 16:
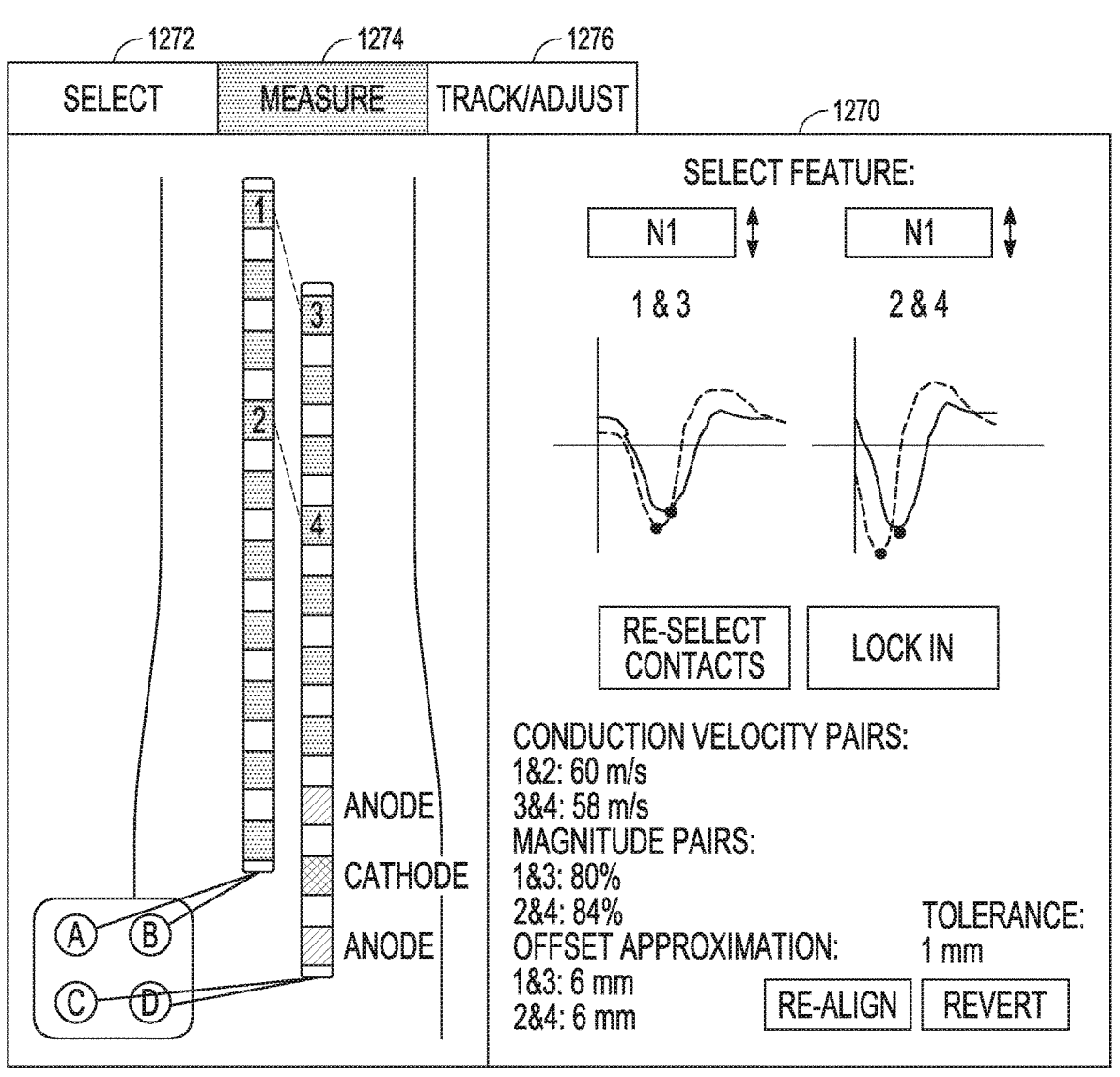
FIG. 16 illustrates an embodiment of a portion of the user interface screen allowing for lead re-alignment during an initial calibration for offset distance measurements.

FIG. 16 illustrates an embodiment of a portion of user
interface screen 1270 allowing for lead re-alignment during
the initial calibration for offset distance measurements. After
the offset distance is determined and the reliability is
assessed, the user can accept the offset distance and enter a
re-alignment command (e.g., by hitting a "re-align" button
in the measurement field on screen 1270). In response, lead
configuration circuit 962 automatically updates the lead
configuration from the locked-in lead configuration using
the determined offset distance (i.e., locks in the newly
determined lead configuration). In a further embodiment,
lead configuration circuit 962 can undo the update in
response to a user revert command (e.g., by hitting a "revert"
button in the measurement field on screen 1270) to revert to
the locked-in lead configuration.

When the lead configuration is ready to saved, such as in
response to a user lock-in command (e.g., when the user hits
a "lock in" button in the measurement field on screen 1270),
lead configuration circuit 962 can store the updated lead
configuration as the locked-in lead configuration. The
locked-in lead configuration is used by stimulation control
circuit 920 for determining the one or more stimulation
waveforms and the one or more stimulation fields.

Figure 17:
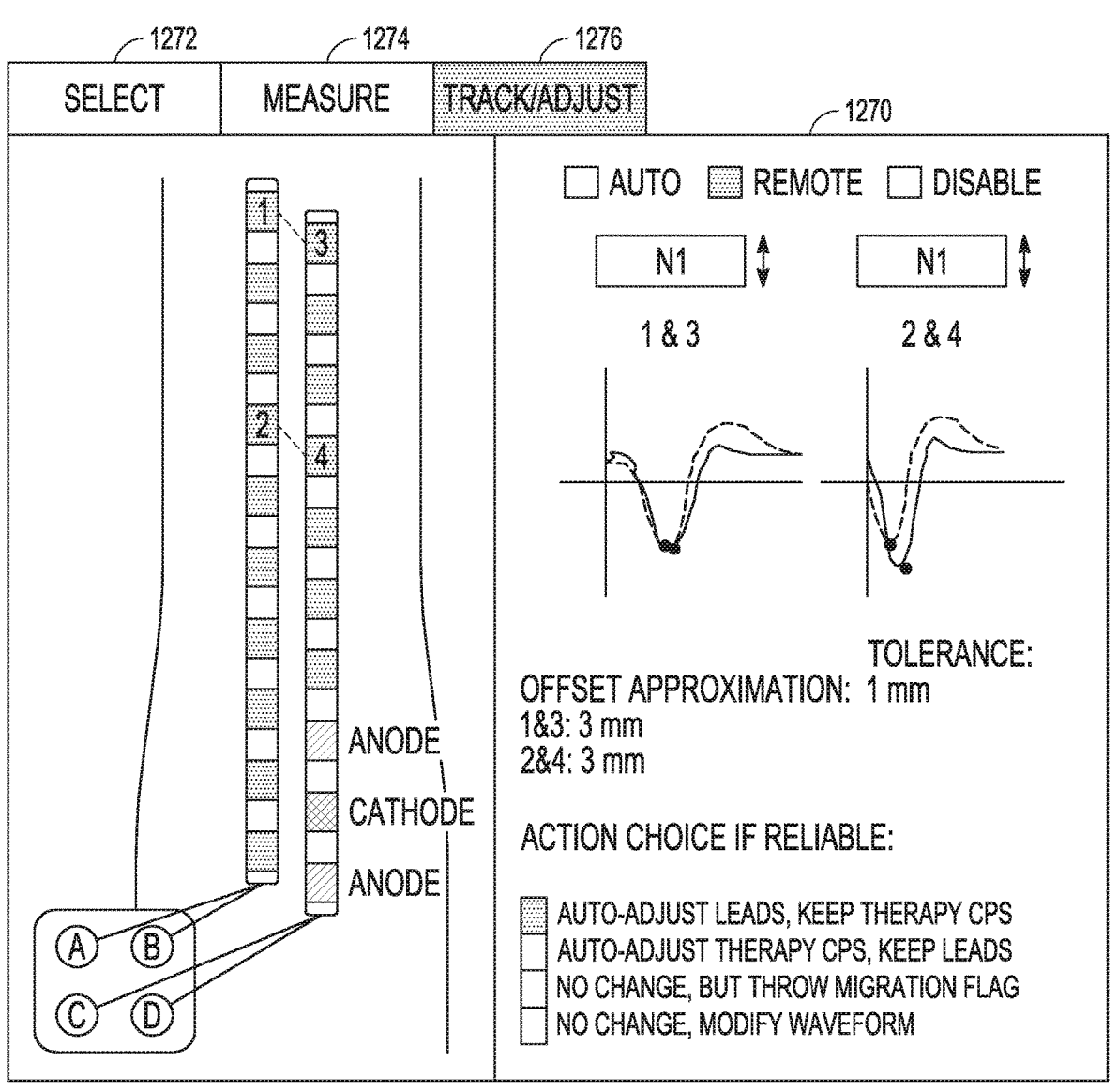
FIG. 17 illustrates an embodiment of a portion of the user interface screen allowing for adjustment of neurostimulation in response to detection of lead migration.

FIG. 17 illustrates an embodiment of a portion of user
interface screen 1270 allowing for adjustment of neuro-
stimulation in response to detection of lead migration. After
one or more offset distances are determined and indicate a
lead migration that may affect efficacy and/or safety of the
neurostimulation, system 960 when implemented in a neu-
rostimulation system allows for tracking of lead migration
based on the offset distances determined over time and
adjustment of the lead configuration based on the lead
migration. When track/adjust tab 1276 is selected, a tracking
and adjustment field (or window) is displayed on screen
1270, as illustrated in FIG. 16.

Lead configuration circuit 962 can determine one or more
initial feature delays at t(0), where t(0) is the time of an
initial measurement for establishing a baseline, for example
during the initial calibration. In various embodiments, lead
configuration circuit 962 measures the one or more feature
delays from sensed neural signals including ECAPs and can
also determine initial ECAP magnitudes at t(0), especially if
positions of the electrodes are referenced to vertebral discs,
to determine and/or verify the one or more feature delays.
Lead configuration circuit 962 can generate the lead con-
figuration based on the one or more feature delays. The lead
configuration can be locked in (e.g., when the user believes
that the one or more feature delays or one or more offset
distances calculated from the one or more feature delays are
reliable) for programming the neurostimulation. Then, lead
configuration circuit 962 can compute one or more current
feature delays at t(1), t(2), . . . t(n), where n is the number
of each measurement and t(n) is the time of the $n^{th}$ mea-
surement. When desired, lead configuration circuit 962 can
also determine current ECAP magnitudes at t(1), t(2), . . .
t(n) to determine and/or verify the one or more current
feature delays. Lead configuration circuit 962 applies mea-
surement settings (e.g., electrode selection and signal feature
selection) determined during the initial calibration (e.g., at
t(0)) to each subsequent measurement (at t(1), t(2), . . . t(n)).

In various embodiments, lead configuration circuit 962
can compare the one or more current feature delays (mea-
sured at t(n)) to the respective the one or more initial feature
delays (measured at t(0)) and/or one or more previous
feature delays (measured at t(m), where m=1, 2, . . . and/or
n−1). When desired, lead configuration circuit 962 can also
compare the one or more current ECAP magnitudes (mea-
sured at t(n)) to the respective the one or more ECAP
magnitudes (measured at t(0)) and/or one or more previous
ECAP magnitudes (measured at t(m), where m=1, 2, . . .
and/or n−1). Such measurements provide for tracking of lead
migration.

In various embodiments, lead configuration circuit 962
can translate the one or more feature delays into one or more
offset distances. When desired, lead configuration circuit
962 can determine the one or more offset distances using
signal magnitudes, which can be used alone for determining
the one or more offset distances or for verifying the one or
more offset distances determined using the one or more
feature delays. Each offset distance determined using a
feature delay and/or signal magnitude is an approximation of
the actual offset distance, with accuracy depending on
sampling rate applied to the sensed signal(s) and other
practical factors related to the measurements.

Lead configuration circuit 962 can start an adjustment
process in response to a measurement that results in an
indication that the lead migration has exceeded an accept-
able degree (e.g., a specified threshold feature delay or offset
distance). In various embodiments, lead configuration cir-
cuit 962 can automatically adjust one or more parameters for the neurostimulation based on the results of the measurement. In various embodiments, lead configuration circuit 962 can inform the user of the results of the measurement and, in response to the user's response, automatically adjust the one or more parameters or allow the user to perform manual adjustment, among other options.

Lead configuration circuit 962 can automatically adjust the presentation of the lead configuration on screen 1270 in response to a change in the measurement results. Lead configuration circuit 962 can also display on screen 1270, or communicate to the user and/or the patient in another manner, a "hint" or a "recommendation" for the next step taken by the user and/or the patient (e.g., when the user has a reason not to allow for an automatic adjustment of the lead configuration and/or the stimulation parameters). In response to a user or patient response accepting the hint or recommendation for automatic adjustment of the stimulation parameters, stimulation control circuit 920 can adjust the stimulation parameters. For example, because the lead migration resulted in shift of the stimulation field, stimulation control circuit 920 can adjust the stimulation field based on the one or more current offset distances such that the one or more offset distances are each within specified offset thresholds or tolerances. The adjustment can include activation or deactivation of one or more electrode and/or adjustment of the fractionalization. In various embodiments, after a new electrode configuration is locked in using lead configuration circuit 962 following new measurements, stimulation control circuit determines new stimulation parameters for reprograming the neurostimulation based on the newly locked in electrode configuration. In various embodiments, the patient can feel the change resulting from the adjustment of the stimulation parameters and can use a patient device (e.g., RC 632) to accept or reject the parameter adjustment.

In various embodiments, stimulation control circuit 920 can determine a response to the change in the measurement results based on the reliability assessment as discussed above. For example, stimulation control circuit 920 can:

present an alert message notifying the user of a lead migration that may require adjustment of the neurostimulation and/or notifying the patient to schedule a re-programing session, without automatically adjusting the stimulation parameters;

automatically adjust the stimulation waveform(s) and/or stimulation field(s) to accommodate the lead migration; or in case of the offset likelihood metric shows low reliability, adjust the stimulation waveform(s) (e.g., amplitude, pulse width, pulse rate) and notify the user and/or the patient, for example:

notify the patient to schedule a re-programing session; or report to the user of suspected lead migration that may need adjustment of the neurostimulation, with measurement results.

FIG. 18 illustrates an embodiment of a method 1800 for detecting lead migration and adjusting neurostimulation based on the detection. Method 1800 can be performed using system 960 when system 960 is implemented in a neurostimulation system such as system 100, 500, or 600, including their various embodiments as discussed in this document. In various embodiments, method 1800 can be performed for delivering neurostimulation to a patient through a plurality of electrodes using first and second leads each including one or more electrodes of the plurality of electrodes.

At 1801, signals are sensed from the patient using a sensing circuit and sensing electrodes selected from the plurality of electrodes. The signals each include a signal feature associated with a response of the patient to the neurostimulation. In one embodiment, the sensed signals include neural signals including ECAPs. At 1802, a pair of respective first and second electrodes are determined for the first and second leads. At 1803, respective first and second signal features are detected from the signals sensed using the first and second electrodes. In one embodiment, neural signals including ECAPs are sensed, and respective ECAP features are detected from the neural signals sensed using the first and second electrodes. In various embodiments, an initial calibration is performed for determining the lead configuration using the feature delay. The performance of the initial calibration includes determining and confirming a selection for the first and second electrodes and determining and confirming a selection for the first and second signal features.

At 1804, a feature delay is detected. The feature delay is a time interval between the detected respective signal features. In various embodiments, the feature delay is used to determine an approximation of an offset distance between the first and second electrodes. During the initial calibration, a conduction velocity can be determined using the detected first and second signal features, the feature delay is measured, and the offset distance between the first and second electrodes can be calculated by multiplying the determined conduction velocity by the measured feature delay.

At 1805, a lead configuration is determined using the feature delay. The lead configuration includes positions of the plurality of electrodes. In various embodiments, the lead configuration is determined using the offset distance (which is determined using the feature delay).

At 1806, one or more stimulation waveforms and one or more stimulation fields are determined based on the lead configuration. The one or more stimulation fields each specify a distribution of a stimulation energy over the plurality of electrodes. In various embodiments, the calculated offset distance can be compared to a specified tolerance. A re-alignment option is recommended in response to the determined offset distance exceeding the specified tolerance. If the recommendation is not accepted, a warning message can be presented. If the recommendation is accepted, the lead configuration can be automatically updated using the measured feature delay or the calculated offset distance. In various embodiments, reliability of the measurements is assessed by determining the offset distance using repeated determination using a single method of determining the offset distance and/or repeated determination using multiple methods of determining the offset distance, and comparing results obtained from determining the offset distance using the repeated determination using the single method and/or the repeated determination using the multiple methods. The assessment of the reliability of the measurements can include assessing a likelihood of lead migration that has actually occurred and/or a reliability of the calculated offset distance. A recommendation for adjustment of one or more stimulation waveforms and/or one or more stimulation fields can be produced based on the assessed reliability of the measurements. At 1807, a plurality of stimulation parameters controlling delivery of the neurostimulation is generated according to the one or more stimulation waveforms and the one or more stimulation fields using one or more processors.

In various embodiments, the determination of the conduction velocity, the detection of the feature delay, and the calculation of the offset distance can be repeated for monitoring lead migration over time using selection of the first and second electrodes and the selection of the first and second signal features determined and confirmed during the initial calibration. The lead migration (e.g., the relative displacement between the first and second leads) can be monitored by tracking values of the offset distance calculated over time.

Figure 19:
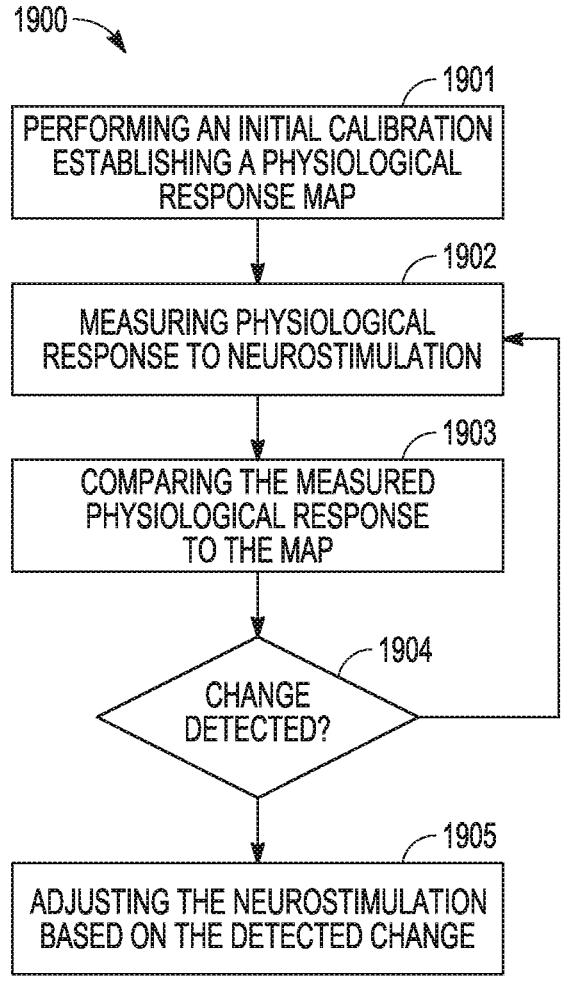
FIG. 19 illustrates an embodiment of a method for detecting changes in physiological response to neurostimulation and adjusting the neurostimulation based on the detection.

FIG. 19 illustrates an embodiment of a method 1900 for detecting changes in physiological response to neurostimulation and adjusting the neurostimulation based on the detection. Method 1800 is an example of method 1900 in which electrical stimulation pulses are delivered and neural electrical responses are sensed. While electrical stimulation pulses and neural electrical responses are specifically discussed above as an example, the present subject matter is applicable to other signal modalities (i.e., stimuli other than electrical pulses and/or responses sensed using signals other than electrical neural activities such as ECAP). The present subject matter can be applied to any system that delivers a stimulation signal to produce a signal propagation that depends on the distance between the stimulation and sensing sites. Examples of such a system can include an optical stimulation in which scattered light is sensed, a thermal stimulation system is which temperature is sensed, and an ultrasound stimulation system in which evoked responses including heat are sensed.

At 1901, an initial calibration is performed. A physiological response map is established is established during the initial calibration. At 1902, physiological response to neurostimulation is measured. At 1903, the measured physiological response is compared to the physiological response map. If no change in physiological response is detected at 1904, monitoring continues from 1902. If a change in physiological response is detected at 1904, stimulation parameters are adjusted based on the detected change at 1905. Steps 1902, 1903, 1904, and 1905 can be repeated to track changes in the system that may require adjustment of the stimulation parameters, such as on a periodic basis or in response to an event such as a change in response to the neurostimulation noticed by the patient.

In various embodiments, the adjustment of the stimulation parameters can be verified with feedback from the patient. In various embodiments, the adjustment of the stimulation parameters can be performed automatically in response to the detected change exceeding a threshold, performed automatically in response to a command from the user or the patient accepting a recommendation for the adjustment, or disabled (e.g., by the user who determines manual adjustment is more appropriate).

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering neurostimulation to a patient through a plurality of electrodes using first and second leads each including one or more electrodes of the plurality of electrodes, the system comprising:
    a programming control circuit configured to generate stimulation parameters controlling delivery of the neurostimulation according to one or more stimulation waveforms and one or more stimulation fields, the one or more stimulation fields each specifying a distribution of a stimulation energy over the plurality of electrodes;
    a sensing circuit configured to sense signals using sensing electrodes selected from the plurality of electrodes; and
    a stimulation control circuit configured to determine the one or more stimulation waveforms and the one or more stimulation fields based on a lead configuration including positions of the plurality of electrodes, the stimulation control circuit including a lead configuration circuit configured to:
        determine a first electrode of the first lead and a second electrode of the second lead;
        receive a first signal sensed using the first electrode and a second signal sensed using the second electrode;
        detect a first signal feature from the first signal and a second signal feature from the second signal, the first and second signal features associated with a response of the patient to the neurostimulation;
        determine a feature delay being a time interval between the detected first and second signal features;
        determine a need for adjusting the lead configuration using the feature delay; and
    a stimulation device configured to deliver the neurostimulation and to control the delivery of the neurostimulation using the generated stimulation parameters.

2. The system of claim 1, wherein the sensing circuit is configured to sense neural signals including evoked compound action potentials (ECAPs), and the lead configuration circuit is configured to detect an ECAP feature from each of the first and second signals as the respective first and second signal features.

3. The system of claim 2, wherein the lead configuration circuit is configured to perform an initial calibration for determining the lead configuration using the feature delay, the initial calibration including determining and confirming a selection for the first and second electrodes and determining and confirming a selection for the first and second signal features, and wherein the system comprises a user interface configured to present the lead configuration and to receive user input for at least one of selecting the first and second electrodes or selecting the first and second signal features.

4. The system of claim 3, wherein the lead configuration circuit is configured to perform measurements automatically for the initial calibration, the measurements determining at least the feature delay.

5. The system of claim 1, wherein the lead configuration circuit is configured to:
    determine a conduction velocity using the detected first and second signal features;
    determine the feature delay;
    calculate an offset distance between the first and second electrodes by multiplying the determined conduction velocity by the determine feature delay; and
    determine the lead configuration using the offset distance.

6. The system of claim 5, wherein the lead configuration circuit is configured to:
    compare the calculated offset distance to a specified tolerance;
    recommend a re-alignment option in response to the determined offset distance exceeding the specified tolerance;
    present a warning message in response to the recommendation not being accepted; and
    automatically update the lead configuration using the calculated offset distance in response to the recommendation being accepted.

7. The system of claim 5, wherein the lead configuration circuit is configured to assess reliability of measurements by determining the offset distance by at least one of repeated determination using a single method of determining the offset distance or repeated determination using multiple methods of determining the offset distance and comparing results obtained from determining the offset distance using the multiple methods.

8. The system of claim 7, wherein the lead configuration circuit is configured to:

determine a morphological parameter of each of the signals sensed using the first and second electrodes;

calculating the offset distance using the determined morphological parameter and template morphological parameter; and assess reliability of the calculated offset distance by comparing the offset distance calculated using the feature delay and the offset distance calculated using the morphological parameter.

9. The system of claim 7, wherein the lead configuration circuit is configured to assess at least one of a likelihood of lead migration that has actually occurred or a reliability of the calculated offset distance.

10. The system of claim 7, wherein the lead configuration circuit is configured to produce a recommendation for adjustment of at least one of the one or more stimulation waveforms or the one or more stimulation fields based on the assessed reliability of the measurements.

11. A method for delivering neurostimulation to a patient through a plurality of electrodes using first and second leads each including one or more electrodes of the plurality of electrodes, the method comprising:

sensing signals using a sensing circuit and sensing electrodes selected from the plurality of electrodes, the signals each including a signal feature associated with a response of the patient to the neurostimulation;

generating a plurality of stimulation parameters controlling delivery of the neurostimulation according to one or more stimulation waveforms and one or more stimulation fields using one or more processors, the one or more stimulation fields each specifying a distribution of a stimulation energy over the plurality of electrodes, the generating including:

determining a pair of respective first and second electrodes for the first and second leads;

detecting first and second signal features from the signals sensed using the first and second electrodes;

determining a feature delay being a time interval between the detected first and second signal features;

determining a need for adjusting a lead configuration using the feature delay, the lead configuration including positions of the plurality of electrodes; and determining the one or more stimulation waveforms and the one or more stimulation fields based on the lead configuration;

programming a stimulation device to control delivery of the neurostimulation using the generated plurality of stimulation parameters; and delivering the neurostimulation using the stimulation device.

12. The method of claim 11, wherein sensing signals comprises sensing neural signals including evoked compound action potentials (ECAPs), and detecting respective signal features from the neural signals sensed using the first and second electrodes comprises detecting respective ECAP features from the neural signals sensed using the first and second electrodes.

13. The method of claim 11, comprising performing an initial calibration for determining the lead configuration using the feature delay, wherein the performance of the initial calibration includes:

determining and confirming a selection for the first and second electrodes; and determining and confirming a selection for the first and second signal features.

14. The method of claim 13, wherein performing the initial calibration comprises:

determining a conduction velocity using the detected first and second signal features;

determining the feature delay;

calculating an offset distance between the first and second electrodes by multiplying the determined conduction velocity by the determined feature delay; and determining the lead configuration using the offset distance.

15. The method of claim 14, wherein performing the initial calibration further comprises:

comparing the calculated offset distance to a specified tolerance;

recommending a re-alignment option in response to the determined offset distance exceeding the specified tolerance;

presenting a warning message in response to the recommendation not being accepted; and automatically updating the lead configuration using the calculated offset distance in response to the recommendation being accepted.

16. The method of claim 14, further comprising assessing reliability of measurements by:

determining the offset distance using at least one of repeated determination using a single method of determining the offset distance or repeated determination using multiple methods of determining the offset distance; and comparing results obtained from determining the offset distance using the at least one of the repeated determination using the single method or the repeated determination using the multiple methods.

17. The method of claim 16, wherein assessing reliability of the measurements comprises assessing at least one of a likelihood of lead migration that has actually occurred or a reliability of the calculated offset distance.

18. The method of claim 17, further comprising producing a recommendation for adjustment of at least one of the one or more stimulation waveforms or the one or more stimulation fields based on the assessed reliability of the measurements.

19. The method of claim 14, further comprising:

repeating the determination of the conduction velocity, the determination of the feature delay, and the calculation of the offset distance using selection of the first and second electrodes and the selection of the first and second signal features determined and confirmed during the initial calibration; and monitoring migration of at least one of the first and second leads based on values of the offset distance calculated over time.

20. A non-transitory computer-readable storage medium including instructions, which when executed by a system, cause the system to perform a method for delivering neurostimulation to a patient through a plurality of electrodes using first and second leads each including one or more electrodes of the plurality of electrodes, the method comprising:

sensing signals using a sensing circuit and sensing electrodes selected from the plurality of electrodes, the signals each including a signal feature associated with a response of the patient to the neurostimulation;
generating a plurality of stimulation parameters controlling delivery of the neurostimulation according to one or more stimulation waveforms and one or more stimulation fields using one or more processors, the one or more stimulation fields each specifying a distribution of a stimulation energy over the plurality of electrodes, the generating including:
  determining a pair of respective first and second electrodes for the first and second leads;
  detecting respective signal features from the signals sensed using the first and second electrodes;
  determining a feature delay being a time interval between the detected respective signal features;
  determining a need for adjusting a lead configuration using the feature delay, the lead configuration including positions of the plurality of electrodes; and
  determining the one or more stimulation waveforms and the one or more stimulation fields based on the lead configuration;
programming a stimulation device to control delivery of the neurostimulation using the generated plurality of stimulation parameters; and
delivering the neurostimulation using the stimulation device.

* * * * *